United States Patent [19]

Groenen et al.

[11] Patent Number: 5,462,862
[45] Date of Patent: Oct. 31, 1995

[54] METHOD AND COMPOSITIONS FOR ENHANCING PRODUCTION OF SECONDARY METABOLITES USING CLUSTERED BIOSYNTHETIC GENES

[75] Inventors: Martinus A. M. Groenen, Zetten; Annemarie E. Veenstra, Vennep; Pieter Van Solingen, Naaldwijk; Bertus P. Koekman, Schipluiden; Lucia H. M. Van Der Voort, Delft, all of Netherlands; Juan F. Martin; Santiago Gutierrez, both of Leon, Spain; Bruno Diez, Sebastian, Spain; Emilio Alvarez, Sevilla, Spain; Jose L. Barredo, Trespaderne, Spain; Christina Esmahan, Bilbao, Spain

[73] Assignee: Gist-brocades N.V., Delft, Netherlands

[21] Appl. No.: 8,688

[22] Filed: Jan. 25, 1993

Related U.S. Application Data

[63] Continuation of Ser. No. 392,119, Aug. 10, 1989, abandoned.

[30] Foreign Application Priority Data

Aug. 11, 1988 [EP] European Pat. Off. ............. 88201714
Apr. 21, 1989 [EP] European Pat. Off. ............. 89201044

[51] Int. Cl.$^6$ .................... C12P 21/06; C12N 15/00; C12N 1/20; C07H 17/00
[52] U.S. Cl. ............... 435/69.1; 435/172.3; 435/252.1; 435/252.3; 435/320.1; 536/23.1; 536/23.4; 536/23.7
[58] Field of Search ..................... 435/69.1, 70.1, 435/172.1, 172.2, 172.3, 252.3, 252.1, 235, 240.2, 320.1, 6; 536/23.1, 23.4, 23.7; 530/350, 371

[56] References Cited

U.S. PATENT DOCUMENTS

4,892,819 1/1990 Carr et al. ............................. 435/69.1
4,950,603 8/1990 Ingolia et al. ......................... 435/235
5,108,918 8/1992 Groenen et al. ..................... 435/172.3

FOREIGN PATENT DOCUMENTS

0260762 3/1988 European Pat. Off. .
0320272 6/1989 European Pat. Off. ......... C12N 15/00

OTHER PUBLICATIONS

Veenstra et al. (1989) Genetics and Molecular Biology of Industrial Microorganisms, ASM, pp. 262–269.

Ballance and Turner, "Development of a High–frequency Transforming Vector for *Aspergillus nidulans*", Gene, vol. 36, pp. 321–331 (1985).

Caltrider and Niss, "Role of Methionine in Cephalosporin Synthesis", *Appl. Microbiol.*, vol. 14, pp. 746–753 (1966).

Chapman et al., "Recombinant DNA Studies in *Cephalosporium acremonium*", Developments in Industrial Microbiol., vol. 27, pp. 165–174 (1987).

Demain, "Biosynthesis of Beta–Lactam Antibiotics", *Antiobiotics Containing the Beta–Lactam Structure I*, pp. 189–228 (1983).

(List continued on next page.)

Primary Examiner—Garnette D. Draper
Assistant Examiner—Gian P. Wang
Attorney, Agent, or Firm—Barbara Rae-Venter

[57] ABSTRACT

Clustered antibiotic biosynthetic genes are employed for improvement of production of the antibiotic in microorganisms and for the isolation of other genes involved in the biosynthesis of the antibiotic. The invention is exemplified with improved production of penicillin in *Penicillium chrysogenum*, with the isolation of another clustered biosynthetic gene(s) and with the expression of penicillin biosynthetic genes in *Acremonium chrysogenum*.

17 Claims, 13 Drawing Sheets

OTHER PUBLICATIONS

Lopez–Nieto et al., "Characterization of the Biosynthesis In Vivo of alpha–aminoadipyl–cysteinyl–valine in *Penicillium chrysogenum*", *Appl. Microbiol. Biotechnol.*, vol. 22, pp. 343–351 (1985).

Alonso et al., "Enzymatic Synthesis of Penicillins", *J. of Antibiotics*, pp. 1074–1084 (1988).

Makins et al., "Genetics of penicillin Producing Organisms", *Advances in Biotechnology*, vol. 3, pp. 51–61 (1980).

Makins et al., "The Genetic Location of Three Mutations Impairing Penicillin Production in *Aspergillus nidulans*", *J. of General Microbiol.*, vol. 129, pp. 3027–3033 (1983).

Malpartida and Hopwood, "Molecular Cloning of the Whole Biosynthetic Pathway of a Streptomyces Antiobiotic and its Expression in a Heterologous Host", *Nature*, vol. 309, pp. 462–464 (1984).

Martin and Liras, "Biosynthesis of beta–Lactam Antiobiotics: Design and Construction of Overproducing Strains", *TIBS*, vol. 3, pp. 39–44 (1985).

Mattern et al., "Transformation of *Aspergillus oryzae* Using the *A. Niger* pyrG Gene", *Mol. Gen. Genet.*, vol. 210, pp. 460–461 (1987).

Messing et al., "New M13 Vectors for Cloning", *Meth. Enzymol.*, vol. 101, pp. 20–79 (1983).

Motamedi et al., "Cloning and Heterologous Expression of a Gene Cluster for the Biosynthesis of Tetracenomycin C", *Proc. Natl. Acad. Sci. USA*, vol. 84, pp. 4445–4449 (1987).

Normansell et al., "Genetic and Biochemical Studies of Mutants of *Penicillium chrosogenum* Impaired in Penicillin Production", *J. of General Microbiol.*, vol. 112, pp. 113–126 (1979).

Punt et al., "Transformation of Aspergillus Based on the Hygromycin B Resistance Marker from *Escherichia coli*", *Gene*, vol. 56, pp. 117–124 (1987).

Ramos et al., "Coordinate Increase of Isopenicillin N Synthetase, Isopenicillin N Epimerase and Deacetoxycephalospor in C Synthetase . . . ", *FEMS Microbiol. Letters*, vol. 35, pp. 123–127 (1986).

Revilla et al., "Glucose Represses Formation of (L–alpha–Aminoadipyl)–L–Cysteinyl–D–Valine and Isopenicillin N Synthase", *J. of Bacteriol.*, vol. 168, pp. 947–952 (1986).

Shirafuji et al., "Accumulation of Tripeptide Derivatives by Mutants of *Cephalosporium acremonium*", *Agric. Bio. Chem.*, vol. 43, pp. 155–160 (1979).

Skatrud et al., "Strain Improvement Studies in *Penicillium chrysogenum* . . . ", Poster Presentation *1987 Annual Meeting of the Society of Industrial Microbiol.* (1987).

Wernars et al., "Cotransformation of *Aspergillus nidulans*: A Tool for Replacing Fungal Genes", *Mol. Gen. Genet.*, vol. 209, pp. 71–77 (1987).

Alvarez et al., "Purification of Homogeneity and Characterization of Acyl Coenzyme A:6–Aminopenicillanic Acid Acyltransferase of *Penicillium Chrysogenum*", *Antimicrob. Agents Chemother.*, pp. 1675–1682 (1987).

|  | 10 | 20 | 30 | 40 | 50 | 60 |
|---|---|---|---|---|---|---|

AAGCTTTCAGGCAACCTAGGCAACCCAATAGGAACCAAGTGATAGGCCCACCTGCTTTCT

```
         70        80        90       100       110       120
ATCTAGTCTGGACGGTTGCTATTGGCTCGATCATTGTTTACCATCCCGGCAAAAAGCTCT 130       140       150       160       170       180
ACAGAGTTGTGCTATTTCTATTCCTGTCTTGGCATGTCCAGGCTGGCTGTTATCGCCTCC 190       200       210       220       230       240
GTGGTGAACCCTCTTCATGCAAGAGGTCAGTCAATAATGCGCTTCACCGTTCTCGACGAA 250       260       270       280       290       300
ACTTGGCATCCATGCTCAATCCAGCTCCTCGGCAAGACTAGGCGGATGCAGCAGGGATAC 310       320       330       340       350       360
TCGAGGTGCCCCAGTTGATGTCCCATCAGTGTCATGCTATGGTCCCAGATTGGTGGCTAC 370       380       390       400       410       420
GGCCAATATAAATCTCAGCATGCAGTTCCGCCTGCATGATCATCCCCAGGACGCGTTTGT 430       440       450       460       470       480
CATCTCCGTCAGCCAGGTCTCAGTTGTTTACCCATCTTCCGACCCGCAGCAGAAATGCTT
                                                        MetLeu 490       500       510       520       530       540
CACATCCTCTGTCAAGGCACTCCCTTTGAAGTAAGTGCTGCACTGAATACCAGATTTTTT
HisIleLeuCysGlnGlyThrProPheGlu 550       560       570       580       590       600
CCTTCTGAATCTTCCGAGTTCTGACCTGATCCAGATCGGCTACGAACATGGCTCTGCTGC
                                    IleGlyTyrGluHisGlySerAlaAl 610       620       630       640       650       660
CAAAGCCGTGATAGCCAGAAGCATTGACTTCGCCGTCGATCTCATCCGAGGGAAAACGAA
aLysAlaValIleAlaArgSerIleAspPheAlaValAspLeuIleArgGlyLysThrLy 670       680       690       700       710       720
GAAGACGGACGAAGAGCTTAAACAGGTACTCTCGCAACTGGGGCGCGTGATCGAGGAAAG
sLysThrAspGluGluLeuLysGlnValLeuSerGlnLeuGlyArgValIleGluGluAr 730       740       750       760       770       780
ATGGCCCAAATACTACGAGGAGATTCGCGGTGAGTGCCACTTCGGTCTTTCCTACATTTT
gTrpProLysTyrTyrGluGluIleArgG
```

FIG. 3A

```
         790       800       810       820       830       840
CTGCACCAATGCTGACCGATGACCCCCGAAAAACCAGGTATTGCAAAGGGCGCTGAACGC
                           lyIleAlaLysGlyAlaGluArg 850       860       870       880       890       900
GATGTCTCCGAGATTGTCATGCTTAATACCCGCACGGAATTTGCATACGGGCTCAAGGCA
AspValSerGluIleValMetLeuAsnThrArgThrGluPheAlaTyrGlyLeuLysAla 910       920       930       940       950       960
GCCCGTGATGGCTGCACCACTGCCTATTGTCAACTTCCAAATGGAGCCCTCCAGGGCCAA
AlaArgAspGlyCysThrThrAlaTyrCysGlnLeuProAsnGlyAlaLeuGlnGlyGln 970       980       990      1000      1010      1020
AACTGGGATGTACGTTAAGAGATTTTACCTCCTCATTTTATTCCATCGAATTTGCGCCGA
AsnTrpAsp 1030      1040      1050      1060      1070      1080
CTAATTTGGTTGTTCAAGTTCTTTTCTGCCACCAAAGAGAACCTGATCCGGTTAACGATC
               PhePheSerAlaThrLysGluAsnLeuIleArgLeuThrIle 1090      1100      1110      1120      1130      1140
CGTCAGGCCGGACTTCCCACCATCAAATTCATAACCGAGGCTGGAATCATCGGGAAGGTT
ArgGlnAlaGlyLeuProThrIleLysPheIleThrGluAlaGlyIleIleGlyLysVal 1150      1160      1170      1180      1190      1200
GGATTTAACAGTGCGGGGGTCGCCGTCAATTACAACGCCCTTCACCTTCAGGGTCTTCGA
GlyPheAsnSerAlaGlyValAlaValAsnTyrAsnAlaLeuHisLeuGlnGlyLeuArg 1210      1220      1230      1240      1250      1260
CCCACCGGAGTTCCTTCGCATATTGCCCTCCGCATAGCGCTCGAAAGCACTTCTCCTTCC
ProThrGlyValProSerHisIleAlaLeuArgIleAlaLeuGluSerThrSerProSer 1270      1280      1290      1300      1310      1320
CAGGCCTATGACCGGATCGTGGAGCAAGGCGGAATGGCCGCCAGCGCTTTTATCATGGTG
GlnAlaTyrAspArgIleValGluGlnGlyGlyMetAlaAlaSerAlaPheIleMetVal 1330      1340      1350      1360      1370      1380
GGCAATGGGCACGAGGCATTTGGTTTGGAATTCTCCCCCACCAGCATCCGAAAGCAGGTG
GlyAsnGlyHisGluAlaPheGlyLeuGluPheSerProThrSerIleArgLysGlnVal 1390      1140      1410      1420      1430      1440
CTCGACGCGAATGGTAGGATGGTGCACACCAACCACTGCTTGCTTCAGCACGGCAAAAAT
LeuAspAlaAsnGlyArgMetValHisThrAsnHisCysLeuLeuGlnHisGlyLysAsn 1450      1460      1470      1480      1490      1500
GAGAAAGAGCTCGATCCCTTACCGGACTCATGGAATCGCCACCAGCGTATGGAGTTCCTC
GluLysGluLeuAspProLeuProAspSerTrpAsnArgHisGlnArgMetGluPheLeu
```

FIG. 3B

```
         1510      1520      1530      1540      1550      1560
   CTCGACGGGTTCGACGGCACCAAACAGGCATTTGCCCAGCTCTGGGCCGACGAAGACAAT
   LeuAspGlyPheAspGlyThrLysGlnAlaPheAlaGlnLeuTrpAlaAspGluAspAsn 1570      1580      1590      1600      1610      1620
   TATCCCTTTAGCATCTGCCGCGCTTACGAGGAGGGCAAGAGCAGAGGCGCGACTCTGTTC
   TyrProPheSerIleCysArgAlaTyrGluGluGlyLysSerArgGlyAlaThrLeuPhe 1630      1640      1650      1660      1670      1680
   AATATCATCTACGACCATGCCCGTAGAGAGGCAACGGTGCGGCTTGGCCGGCCGACCAAC
   AsnIleIleTyrAspHisAlaArgArgGluAlaThrValArgLeuGlyArgProThrAsn 1690      1700      1710      1720      1730      1740
   CCTGATGAGATGTTTGTCATGCGGTTTGACGAGGAGGACGAGAGGTCTGCGCTCAACGCC
   ProAspGluMetPheValMetArgPheAspGluGluAspGluArgSerAlaLeuAsnAla 1750      1760      1770      1780      1790      1800
   AGGCTTTGAAGGCTCTTCATGACGAGCCAATGCATCTTTTGTATGTAGCTTCAACCGACT
   ArgLeuEnd 1810      1820      1830      1840      1850      1860
   CCGTCTTCACTTCTTCGCCCGCACTGCCTACCGTTTGTACCATCTGACTCATATAAATGT 1870      1880      1890      1900      1910      1920
   CTAGCCCCTACCTACACTATACCTAAGGGAGAGAAGCGTAGAGTGATTAACGTACGGGCC 1930      1940      1950      1960      1970      1980
   TATAGTACCCCGATCTCTAGATAGAACATTTAGTAGAGATTAGGATGCCTAACTAATTTA 1990      2000      2010      2020      2030      2040
   ACTTGAGCATTGTCCCGTTCATATTGATTTTCAGTCCATTATACACTCTTAATCGTTTCC 2050      2060      2070      2080      2090      2100
   CGGTAGAAGCCTGATATATACGACCATAGGGTGTGGAGAACAGGGCTTCCCGTCTGCTTG 2110      2120      2130      2140      2150      2160
   GCCGTACTTAAGCTATATATTCTACACGGCCAATACTCAATGTGCCCTTAGCACCTAAGC 2170      2180      2190      2200      2210      2220
   GGCACTCTAGGGTAAGTGCGGGTGATATAGGTGAGAAGTCTTAAGACTGAAGACAGGATA 2230      2240      2250      2260      2270      2280
   TCACGCGTTACCCTGCACCGTACCTACTACCTTCAATATCAACTCTTTCAGGATGGACAG

GGTCGAC
```

FIG. 3C

SEQUENCE LISTING ( 1 ) GENERAL INFORMATION:

( i i i ) NUMBER OF SEQUENCES: 6

( 2 ) INFORMATION FOR SEQ ID NO: 1:

( i ) SEQUENCE CHARACTERISTICS:

(A) LENGTH: 2287
(B) TYPE: nucleic acid
(C) STRANDEDNESS: single
(D) TOPOLOGY: linear (xi) SEQUENCE DESCRIPTION: SEQ ID NO: 1:

| | | | | | | |
|---|---|---|---|---|---|---|
| AAGCTTTCAG | GCAACCTAGG | CAACCCAATA | GGAACCAAGT | GATAGGCCCA | CCTGCTTTCT | 60 |
| ATCTAGTCTG | GACGGTTGCT | ATTGGCTCGA | TCATTGTTTA | CCATCCCGGC | AAAAAGCTCT | 120 |
| ACAGAGTTGT | GCTATTTCTA | TTCCTGTCTT | GGCATGTCCA | GGCTGGCTGT | TATCGCCTCC | 180 |
| GTGGTGAACC | CTCTTCATGC | AAGAGGTCAG | TCAATAATGC | GCTTCACCGT | TCTCGACGAA | 240 |
| ACTTGGCATC | CATGCTCAAT | CCAGCTCCTC | GGCAAGACTA | GGCGGATGCA | GCAGGGATAC | 300 |
| TCGAGGTGCC | CCAGTTGATG | TCCCATCAGT | GTCATGCTAT | GGTCCCAGAT | TGGTGGCTAC | 360 |
| GGCCAATATA | AATCTCAGCA | TGCAGTTCCG | CCTGCATGAT | CATCCCCAGG | ACGCGTTTGT | 420 |
| CATCTCCGTC | AGCCAGGTCT | CAGTTGTTTA | CCCATCTTCC | GACCCGCAGC | AGAAATGCTT | 480 |
| CACATCCTCT | GTCAAGGCAC | TCCCTTTGAA | GTAAGTGCTG | CACTGAATAC | CAGATTTTTT | 540 |
| CCTTCTGAAT | CTTCCGAGTT | CTGACCTGAT | CCAGATCGGC | TACGAACATG | GCTCTGCTGC | 600 |
| CAAAGCCGTG | ATAGCCAGAA | GCATTGACTT | CGCCGTCGAT | CTCATCCGAG | GAAAACGAA | 660 |
| GAAGACGGAC | GAAGAGCTTA | ACAGGTACT | CTCGCAACTG | GGCGCGTGA | TCGAGGAAAG | 720 |
| ATGGCCCAAA | TACTACGAGG | AGATTCGCGG | TGAGTGCCAC | TTCGGTCTTT | CCTACATTTT | 780 |
| CTGCACCAAT | GCTGACCGAT | GACCCCCGAA | AAACCAGGTA | TTGCAAAGGG | CGCTGAACGC | 840 |
| GATGTCTCCG | AGATTGTCAT | GCTTAATACC | CGCACGGAAT | TTGCATACGG | GCTCAAGGCA | 900 |
| GCCCGTGATG | GCTGCACCAC | TGCCTATTGT | CAACTTCCAA | ATGGAGCCCT | CCAGGGCCAA | 960 |
| AACTGGGATG | TACGTTAAGA | GATTTTACCT | CCTCATTTTA | TTCCATCGAA | TTTGCGCCGA | 1020 |
| CTAATTTGGT | TGTTCAAGTT | CTTTTCTGCC | ACCAAAGAGA | ACCTGATCCG | GTTAACGATC | 1080 |
| CGTCAGGCCG | GACTTCCCAC | CATCAAATTC | ATAACCGAGG | CTGGAATCAT | CGGGAAGGTT | 1140 |
| GGATTTAACA | GTGCGGGGGT | CGCCGTCAAT | TACAACGCCC | TTCACCTTCA | GGGTCTTCGA | 1200 |
| CCCACCGGAG | TTCCTTCGCA | TATTGCCCTC | CGCATAGCGC | TCGAAAGCAC | TTCTCCTTCC | 1260 |
| CAGGCCTATG | ACCGGATCGT | GGAGCAAGGC | GGAATGGCCG | CCAGCGCTTT | TATCATGGTG | 1320 |
| GGCAATGGGC | ACGAGGCATT | TGGTTTGGAA | TTCTCCCCCA | CCAGCATCCG | AAAGCAGGTG | 1380 |
| CTCGACGCGA | ATGGTAGGAT | GGTGCACACC | AACCACTGCT | TGCTTCAGCA | CGGCAAAAAT | 1440 |
| GAGAAAGAGC | TCGATCCCTT | ACCGGACTCA | TGGAATCGCC | ACCAGCGTAT | GGAGTTCCTC | 1500 |
| CTCGACGGGT | TCGACGGCAC | CAAACAGGCA | TTTGCCCAGC | TCTGGGCCGA | CGAAGACAAT | 1560 |
| TATCCCTTTA | GCATCTGCCG | CGCTTACGAG | GAGGGCAAGA | GCAGAGGCGC | GACTCTGTTC | 1620 |
| AATATCATCT | ACGACCATGC | CCGTAGAGAG | GCAACGGTGC | GGCTTGGCCG | GCCGACCAAC | 1680 |
| CCTGATGAGA | TGTTTGTCAT | GCGGTTTGAC | GAGGAGGACG | AGAGGTCTGC | GCTCAACGCC | 1740 |
| AGGCTTTGAA | GGCTCTTCAT | GACGAGCCAA | TGCATCTTTT | GTATGTAGCT | TCAACCGACT | 1800 |
| CCGTCTTCAC | TTCTTCGCCC | GCACTGCCTA | CCGTTTGTAC | CATCTGACTC | ATATAAATGT | 1860 |
| CTAGCCCCTA | CCTACACTAT | ACCTAAGGGA | GAGAAGCGTA | GAGTGATTAA | CGTACGGGCC | 1920 |
| TATAGTACCC | CGATCTCTAG | ATAGAACATT | TAGTAGAGAT | TAGGATGCCT | AACTAATTTA | 1980 |
| ACTTGAGCAT | TGTCCGTTC | ATATTGATTT | TCAGTCCATT | ATACACTCTT | AATCGTTTCC | 2040 |
| CGGTAGAAGC | CTGATATATA | CGACCATAGG | GTGTGGAGAA | CAGGGCTTCC | CGTCTGCTTG | 2100 |
| GCCGTACTTA | AGCTATATAT | TCTACACGGC | CAATACTCAA | TGTGCCCTTA | GCACCTAAGC | 2160 |

```
GGCACTCTAG GGTAAGTGCG GGTGATATAG GTGAGAAGTC TTAAGACTGA AGACAGGATA      2220

TCACGCGTTA CCCTGCACCG TACCTACTAC CTTCAATATC AACTCTTTCA GGATGGACAG      2280

GGTCGAC                                                                2287
```

( 2 ) INFORMATION FOR SEQ ID NO: 2:

( i ) SEQUENCE CHARACTERISTICS:
        ( A ) LENGTH: 355
        ( B ) TYPE: amino acid
        ( C ) STRANDEDNESS: Not Relevant
        ( D ) TOPOLOGY: Not Relevant ( x i ) SEQUENCE DESCRIPTION: SEQ ID NO: 2:

```
His Ile Leu Cys Gln Gly Thr Pro Phe Glu Ile Gly Tyr Glu His Gly
                 5                  10                  15
Ser Ala Ala Lys Ala Val Ile Ala Arg Ser Ile Asp Phe Ala Val Asp
             20                  25                  30
Leu Ile Arg Gly Lys Thr Lys Thr Asp Glu Glu Leu Lys Gln Val
         35                  40                  45
Leu Ser Gln Leu Gly Arg Val Ile Glu Glu Arg Trp Pro Lys Tyr Tyr
     50                  55                  60
Glu Glu Ile Arg Gly Ile Ala Lys Gly Ala Glu Arg Asp Val Ser Glu
 65                  70                  75                  80
Ile Val Met Leu Asn Thr Arg Thr Glu Phe Ala Tyr Gly Leu Lys Ala
                 85                  90                  95
Ala Arg Asp Gly Cys Thr Thr Ala Tyr Cys Gln Leu Pro Asn Gly Ala
            100                 105                 110
Leu Gln Gly Gln Asn Tyr Asp Phe Phe Ser Ala Thr Lys Glu Asn Leu
        115                 120                 125
Ile Arg Leu Thr Ile Arg Gln Ala Gly Leu Pro Thr Ile Lys Phe Ile
    130                 135                 140
Thr Glu Ala Gly Ile Ile Gly Lys Val Gly Phe Asn Ser Ala Gly Val
145                 150                 155                 160
Ala Val Asn Tyr Asn Ala Leu His Leu Gln Gly Leu Arg Pro Thr Gly
                165                 170                 175
Val Pro Ser His Ile Ala Leu Arg Ile Ala Leu Glu Ser Thr Ser Pro
            180                 185                 190
Ser Gln Ala Tyr Asp Arg Ile Val Glu Gln Gly Gly Met Ala Ala Ser
        195                 200                 205
Ala Phe Ile Met Val Gly Asn Gly His Glu Ala Phe Gly Leu Glu Phe
    210                 215                 220
Ser Pro Thr Ser Ile Arg Lys Gln Val Leu Asp Ala Asn Gly Arg Met
225                 230                 235                 240
Val His Thr Asn His Cys Leu Leu Gln His Gly Lys Asn Glu Lys Glu
                245                 250                 255
Leu Asp Pro Leu Pro Asp Ser Trp Asn Arg His Gln Arg Met Glu Phe
            260                 265                 270
Leu Leu Asp Gly Phe Asp Gly Thr Lys Gln Ala Phe Ala Gln Leu Trp
        275                 280                 285
Ala Asp Glu Asp Asn Tyr Pro Phe Ser Ile Cys Arg Ala Tyr Glu Glu
    290                 295                 300
Gly Lys Ser Arg Gly Ala Thr Leu Phe Asn Ile Ile Tyr Asp His Ala
305                 310                 315                 320
Arg Arg Glu Ala Thr Val Arg Leu Gly Arg Pro Thr Asn Pro Asp Glu
                325                 330                 335
```

Met Phe Val Met Arg Phe Asp Glu Glu Asp Glu Arg Ser Ala Leu Asn
                340                 345                 350

Ala Arg Leu
        355

(2) INFORMATION FOR SEQ ID NO: 3:

(i) SEQUENCE CHARACTERISTICS:
        (A) LENGTH: 18
        (B) TYPE: amino acid
        (C) STRANDEDNESS: Not Relevant
        (D) TOPOLOGY: Not Relevant (xi) SEQUENCE DESCRIPTION: SEQ ID NO: 3:

Thr Thr Ala Tyr Cys Gln Leu Pro Asn Gly Ala Leu Gln Gly Gln Asn
                5                   10                  15

Trp Asp (2) INFORMATION FOR SEQ ID NO: 4:

(i) SEQUENCE CHARACTERISTICS:
        (A) LENGTH: 26
        (B) TYPE: amino acid
        (C) STRANDEDNESS: Not Relevant
        (D) TOPOLOGY: Not Relevant (xi) SEQUENCE DESCRIPTION: SEQ ID NO: 4:

Met Leu His Ile Leu Xaa Gln Gly Thr Pro Phe Glu Ile Gly Tyr Glu
                5                   10                  15

His Gly Ser Ala Ala Lys Ala Val Ile Ala
            20                  25

(2) INFORMATION FOR SEQ ID NO: 5:

(i) SEQUENCE CHARACTERISTICS:
        (A) LENGTH: 26
        (B) TYPE: amino acid
        (C) STRANDEDNESS: Not Relevant
        (D) TOPOLOGY: Not Relevant (xi) SEQUENCE DESCRIPTION: SEQ ID NO: 5:

Thr Thr Ala Tyr Cys Gln Leu Pro Asp Gly Ala Leu Gln Gly Gln Asn
                5                   10                  15

Trp Asp Phe Phe Ser Ala Thr Lys Glu Ala
            20                  25

(2) INFORMATION FOR SEQ ID NO: 6:

(i) SEQUENCE CHARACTERISTICS:
        (A) LENGTH: 46
        (B) TYPE: nucleic acid
        (C) STRANDEDNESS: single
        (D) TOPOLOGY: linear (xi) SEQUENCE DESCRIPTION: SEQ ID NO: 6:

GGAACGGCAC TGGTCAACTT GGCCATGGTG GGTAGTTAAT GGTATG                     46

METHOD AND COMPOSITIONS FOR ENHANCING PRODUCTION OF SECONDARY METABOLITES USING CLUSTERED BIOSYNTHETIC GENES

CROSS REFERENCE TO RELATED APPLICATIONS

This application is a continuation f U.S. application Ser. No. 07/392,119, filed Aug. 10, 1989, now abandoned.

TECHNICAL FIELD

The subject field concerns the isolation and use of clustered biosynthetic genes for the production of secondary metabolites.

BACKGROUND AND RELEVANT LITERATURE

As a result of classical strain improvements, penicillin production has increased enormously over the last four decades. These classical strain improvements were primarily based on random mutagenic treatments of *Pencillium chrysogenum* and subsequent selection for mutants that produced more penicillin. The development of cloning techniques however has added a potentially powerful new tool to further improve penicillin production in this fungus.

Penicillin is produced by the filamentous fungus *P. chrysogenum* in several enzymatic steps (e.g. E. Alvarez et al., Antimicrob. Agents Chemother. 31 (1987) pp. 1675–1682). These steps are shown in FIG. 1. Throughout this specification is meant by genes directly involved in the biosynthetic pathway, those genes that encode the enzymes active in the several steps leading to the production of a secondary metabolite, so in case of the production of penicillin G or V, the genes encoding the enzymes shown in FIG. 1 are meant. The first reaction is the formation of the tripeptide δ-(L-α-aminoadipyl)-L-cysteinyl-D-valine from α-amino adipic acid, cysteine and valine. The enzyme that is responsible for this reaction is the ACV synthetase (hereinafter referred to as ACVS), a large multifunctional enzyme. The tripeptide is cyclised by the action of the isopenicillin N synthetase (hereinafter referred to as IPNS) or cyclase. The reaction product is isopenicillin N, a compound that contains the typical β-lactam ring structure and that possesses antibacterial activity. The final step in the formation of penicillin is the exchange of the α-aminoadipic acid side chain of isopenicillin N by a hydrophobic side chain. The hydrophobic side chains commonly used in industrial production are phenylacetic acid, yielding penicillin G and phenoxyacetic acid, yielding penicillin V. The side chain exchange has been proposed to be a reaction catalysed by a single enzyme (A. L. Demain (1983) in: A. L. Demain and N. A. Solomon (ed), Antibiotics containing the β-lactam structure I. Springer Verlag, Berlin; pp. 189–228). However, a two step reaction involving 6-APA as an intermediate is also possible (E. Alvarez et al., vide supra). The enzyme that has been identified to be involved in the final reaction is the acylCoA: 6-APA acyltransferase (hereinafter referred to as AT); this enzyme has been purified to homogeneity (E. Alvarez et al., vide supra). The involvement of a second enzyme, catalysing the reaction from IPN to 6-APA, cannot yet be confirmed nor excluded.

It is not clear either whether one or more enzymatic reactions are rate limiting in the process of penicillin biosynthesis, and if so, which enzymatic steps are involved.

Since the penicillin biosynthetic route begins with three amino acids, which each in their turn are part of other metabolic routes, regulatory steps in these routes will also influence the biosynthesis of penicillin. On the other hand, the production of penicillin is subject to a complex mechanism of carbon catabolite repression and nitrogen source control (J. F. Martin et al. In: H. Kleinkauf, H. von Döhren, H. Donnauer and G. Nesemann (eds), Regulation of secondary metabolite formation. VCH Verlaggesellschaft, Weinheim (1985), pp. 41–75). Regulatory proteins may also be involved in these types of regulation. These regulatory proteins and the proteins regulated by them are defined to be indirectly involved in the biosynthetic pathway of a secondary metabolite, in this case penicillin.

Until recently, the gene of only one of the enzymes active in the biosynthetic pathway to penicillin G, the isopenicillin N synthetase (IPNS) or cyclase, had been cloned and sequenced (L. G. Carr et al., Gene 48 (1986) pp. 257–266), using the corresponding *Acremonium chrysogenum* gene (S. M. Samson et al. Nature 318 (1985) pp. 191–194). The latter gene was cloned and identified by purifying the IPNS protein, determining the amino-terminal amino acid sequence, preparing a set of synthetic oligodeoxyribonucleotides according to this sequence and probing a cosmid genomic library with these mixed oligodeoxyribonucleotides (S. M. Samson, vide supra).

The isolated genes encoding IPNS from both *Penicillium chrysogenum* and *Acremonium chrysogenum* have been used for strain improvement. In *Penicillium chrysogenum* an enhanced enzyme activity has been demonstrated; however no stimulation of penicillin biosynthesis has been found (P. L. Skatrud et al, Poster presentation 1987 annual meeting of the Society of Industrial Microbiology, Baltimore, August 1987, Abstract published in SIM News 37 (1987) pp. 77). In *Acremonium chrysogenum* similar results have been obtained (J. L. Chapman et al, (1987), in: Developments in Industrial Microbiology, Vol. 27, G. Pierce (ed), Society of Industrial Microbiology; S. W. Queener, 4th ASM conference on the Genetics and Molecular Biology of Industrial Microorganisms, Bloomington, October 1988, Proceedings will appear in 1989).

Therefore, up to now no evidence has been obtained that the IPNS gene can be used to obtain increased production of penicillin or cephalosporin by gene amplification.

It has been documented that the biosynthesis of β-lactam antibiotics is subject to glucose repression (J. F. Martin and P. Liras, TIBS 3 (1985), pp. 39–44). This repression by glucose has been unequivocally established for the formation of the tripeptide by the ACVS and for the activity of the IPNS (Revilla et al., J. Bact. 168 (1986), pp. 947–952). For acyltransferase, on the other hand, the data are less convincing. Revilla et al (vide supra) report that AT is not subjected to glucose repression, but other data suggest that AT activity is absent, or at least decreased, in the presence of glucose (B. Spencer and T. Maung, Proc. Biochem. Soc. 1970, pp. 29–30).

It is unknown at which stage of the expression the repression by glucose is exerted; this can be at the transcriptional or at the translational level. If the former regulation applies, differences in mRNA levels between producing and non-producing cultures could be employed to isolate genes, involved in the biosynthesis of penicillin. This method for the isolation of genes involved in the biosynthesis of secondary metabolites is the subject of U.S. Pat. No. 5,108,918, issued Apr. 28, 1992, entitled: "A method for identifying and using biosynthetic or regulatory genes for enhanced production of secondary metabilites" and which is incorporated here by reference.

Clustering of antibiotic biosynthetic genes has been described for Streptomycetes. Some examples are the clustering of the genes involved in the biosynthesis of actinorhodin by *S. coelicolor* (F. Malpartida and D. A. Hopwood, 1984, Nature 309, 462–464) or in the biosynthesis of tetracenomycin C by *S. glaucescens* (H. Motamedi and C. R. Hutchinson, 1987, Proc. Natl. Acad. Sci. U.S.A. 84, 4445–4449).

In fungi, the gene organization of β-lactam biosynthetic genes has been investigated by genetic analysis of mutants, impaired in penicillin biosynthesis. In *Aspergillus nidulans*, four loci have been identified that are involved in penicillin biosynthesis (npe A, B, C and D); these loci have been positioned on four different linkage groups (i.e. chromosomes), viZ. VI, IV, III and II, respectively (J. F. Makins et al., 1980, Advances in Biotechnology 3, 51–60; J. F. Makins et al, 1983, Journal of General Microbiology 129, 3027–3033). In *Penicillium chrysogenum* five loci have been identified (npe V, W, X, Y and Z), these loci have been positioned on three linkage groups, viz. I (npe W, Y, Z) and two others containing npe V and npe X, respectively (P. J. M. Normansell et al, 1979, Journal of General Microbiol. 112, 113–126; J. F. Makins et al, 1980, vide supra). The mutations affecting the ringclosure enzyme (IPNS or cyclase; npe W) and the side chain exchange enzyme (acyltransferase, npe V) are reported to be in separate linkage groups. Hence, the genetic data predict that at least some penicillin biosynthetic genes are spread over the fungal genomes, and clustering of e.g. the cyclase and acyltransferase genes is definitely not anticipated based on these data.

SUMMARY OF THE INVENTION

Clustered antibiotic biosynthetic genes are disclosed and are advantageously employed for improvement of production of the antibiotic in microorganisms and for the isolation of other genes involved in the biosynthesis of the antibiotic. The invention is exemplified with improved production of penicillin in *Penicillium chrysogenum*, with the isolation of another clustered biosynthetic gene(s) and with the expression of clustered penicillin biosynthetic genes in *Acremonium chrysogenum*.

Figure 1:
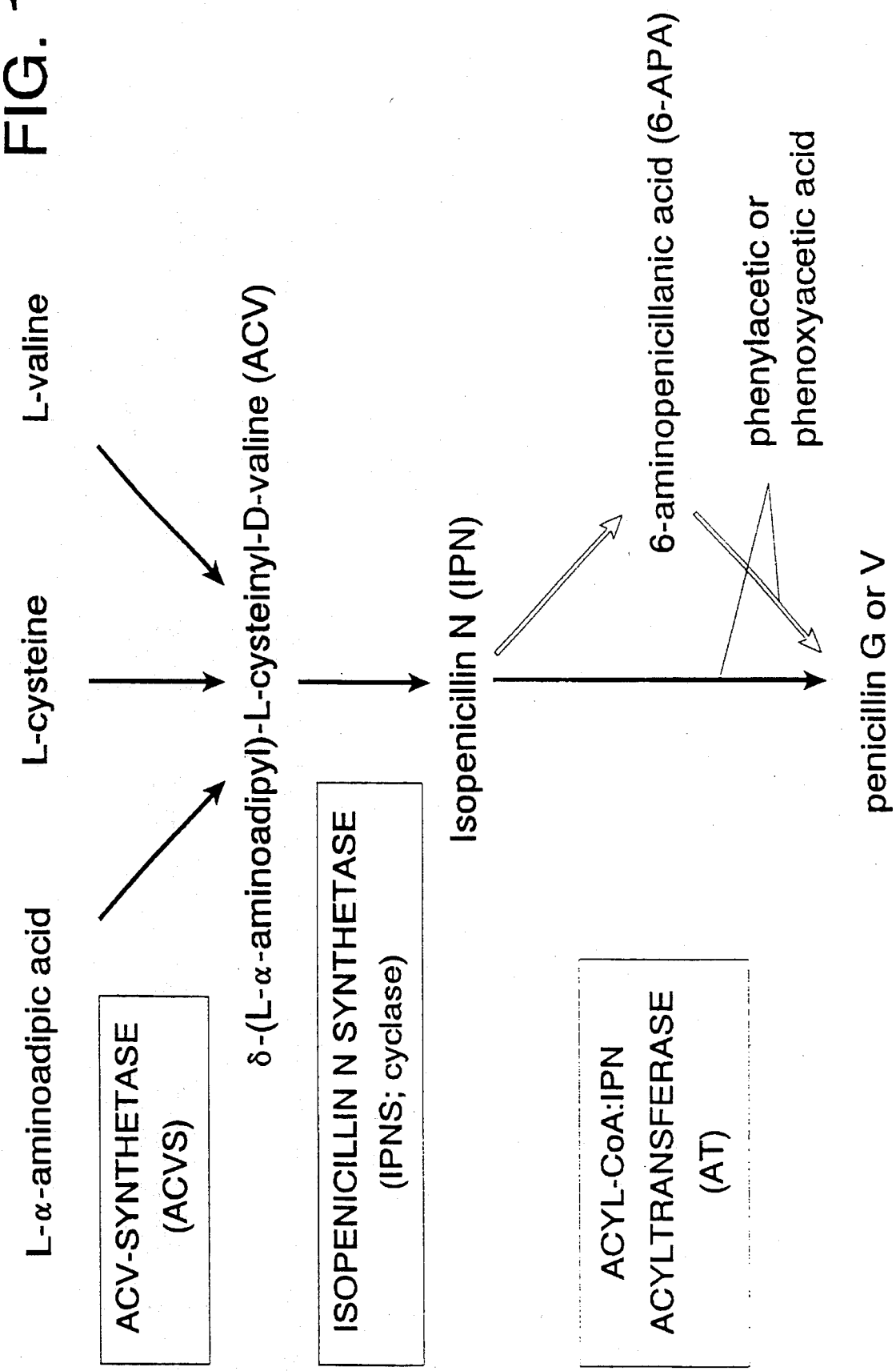
FIG. 1

The biosynthetic pathway to penicillin G or V in *P. chrysogenum* is shown schematically.

FIG. 2

Physical map of the lambda clones G2 and B21 containing the [IPNS plus AT] gene cluster. E=EcoRI; B=BamHI; C=ClaI; H=HindIII; K=KpnI; S=SalI; Sa=SacI; Sp=SphI; P=PstI; X=XhoI; Xb=XbaI; Hp=HpaI; N=NcoI; Bg=BglII. ▬=right arm of bacteriophage lambda EMBL3 (9 kb) ▭=left arm of bacteriophage lambda EMBL3 (20.3 kb)

FIG. 3A–3C

Nucleotide sequence (SEQ ID NO: 1) and deduced amino acid sequence (SEQ ID NO: 2) of the *P. chrysogenum* acyltransferase gene.

FIG. 4

A restriction site and functional map of the cosmid cloning vector pPS07.

FIG. 5

A restriction site and functional map of pPS47.

FIGS. 6A–6B

A restriction site and functional map of pGJ01 A and B.

FIGS. 7A–7B

A restriction site and functional map of pGJ02 A and B.

FIG. 8

A restriction site and functional map of cosmid HM193 (not all sites present are indicated in this map, the interrupted line indicates a less well characterized region).

FIG. 9

Graphical representation of penicillin production by hosts transformed with either pPS47  or pGJ02A .

DESCRIPTION OF THE SPECIFIC EMBODIMENTS

In accordance with the subject invention, DNA fragments are identified which include sequences which are mono- or polycistronic. The genes encoded by the sequences are translated to enzymes concerned with the production of secondary metabolites or other products of commercial interest. These sequences of interest are identified by comparison of DNA sequences isolated from an organism competent to produce the secondary metabolite, where the genes of interest are actively expressed, and a microorganism in which expression is silent. Therefore DNA fragments are provided encoding one or more genes that are differentially expressed and that are involved in the formation of a product of commercial interest. Differentially expressed is used throughout this application for expression of the gene(s) of interest that is specifically active only under certain defined conditions and that is absent (which is meant in this specification to be present at al low level e.g. a level of 5% or less, as compared to the active stage) under other, equally well defined conditions.

The absence of expression may be a result of repression or lack of induction of gene expression, mutation, or any other events which result in transcriptional silence of the gene(s) of interest. The DNA which is isolated may result from screening a gene library, either genomic or cDNA library contained in e.g. a lambda or a cosmid cloning vector or in an expression vector. By employing a cDNA probe enriched for sequences expressed during the biosynthesis of secondary metabolites, positive hybrids may be identified in the library for subsequent manipulation to provide for expression constructs for the enzyme(s) associated with the production of the secondary metabolite. Therefore a gene library of a microorganism is screened using two cDNA probes, one of which is enriched for sequences from the transcriptionally active state and the other is derived from the transcriptionally silent situation. By comparison and subtraction those clones that contain gene(s) that are actively expressed under the defined active conditions only, can be isolated.

The method is exemplified by the isolation of genes involved in the biosynthesis of a secondary metabolite, more specifically penicillin, using two cDNA probes, from lactose grown (producing) and glucose grown (non-producing) mycelium.

By the application of said method, surprisingly, clustered penicillin biosynthetic genes, encoding cyclase and acyltransferase have been isolated from *P. chrysogenum* (cf. our copending application, vide supra). This information can be used advantageously in the isolation of other genes from the said antibiotic biosynthetic pathway by application of the chromosome walking technique known in the art. This latter method finds particular use in cases that the genes of interest are not differentially expressed, that the enzyme encoded by the gene, resists purification which is required for isolation of the gene by the method of "reversed genetics", or that other methods known in the art for the isolation of genes, fail to yield the gene of interest.

Clustering is used throughout this application for the presence of two or more genes with a related function (e.g. involvement in a secondary metabolite biosynthetic pathway) on one DNA fragment that is clonable into a cosmid cloning vector, no other non-related genes being present in between.

Said cluster can represent the natural situation or, in another aspect of the invention, be introduced artificially by combining two or more related genes into one DNA fragment, using the techniques known in the art.

Successful application of the use of the clustering of penicillin biosynthetic genes for the isolation of other penicillin biosynthetic gene is herein exemplified by the isolation by chromosome walking of the gene encoding ACV synthetase.

Moreover, the clustering of penicillin biosynthetic genes has advantageously been used for the amplification of both the cyclase and the acyltransferase genes in *P. chrysogenum*, which results in an increased production of penicillin.

The identified DNA sequences will comprise at least one gene, preferably two or more genes, encoding an antibiotic biosynthetic enzyme and/or a regulatory protein from the entire biosynthetic pathway, or more generally any protein that is involved in whatever way, either positive or negative, in the biosynthesis of said antibiotic.

The positively acting constructs, when properly introduced into a suitable host microorganism increase the efficiency of the biosynthetic pathways operative in β-lactam producing microorganisms by increased gene dosage, or by higher gene expression. On the other hand, constructs may be isolated that have a negative effect on the antibiotic production (e.g. formation of side products). These constructs are employed to inactivate the negatively acting gene by gene replacement or other methods with a similar effect. Both uses result in higher yields of the desired antibiotic during industrial production. This method is exemplified by and finds particular application with β-lactam producing microorganisms for the production of antibiotics, particularly penicillins. Preferably, the expression cassette will include genes encoding enzymes that catalyze rate-limiting steps or genes encoding regulatory proteins for induction of transcription or otherwise.

The subject method further provides sequences for which the encoded product is not known, but the sequence is found to provide an enhanced yield of a desired product. These sequences are referred to as "cryptic genes", which means sequences obtainable by isolation methods described herein, which sequences encompass genes for which no known function is yet assignable. These genes are characterized by being dosed and/or expressed in higher amounts in the transformed host-microorganisms as compared with their untransformed hosts. In addition to the "cryptic genes" and IPNS and acyltransferase, from our copending patent application (vide supra) the present invention provides the gene encoding the first enzyme from the biosynthetic route to penicillin, cephalosporin and cephamycin, viz. the δ-(L-α-aminoadipyl)-L-cysteinyl-D-Valine Synthetase, hereinafter referred to as ACVS.

In the said copending application, a cryptic gene named "Y" was shown to provide enhanced biosynthesis of penicillin. The present invention provides increased production of penicillin by the amplification of the IPNS plus AT gene cluster.

The microorganisms employed in the subject invention include both prokaryotes and eukaryotes, including bacteria such as those belonging to the taxonomic group of the Actinomycetes or Flavobacterium, or fungi (including yeasts), belonging to the genera Aspergillus, Acremonium or Penicillium.

Depending upon the source of the fragment, either genomic or cDNA, either prokaryotic or eukaryotic, various expression cassettes may be constructed. With genomic DNA from a bacterium, the fragment containing a mono- or polycistronic coding region may include its own transcriptional initiation regulatory region, as well as a transcriptional termination region and appropriate translational signals, e.g. Shine-Delgarno sequence and stop codons. Where the genomic DNA is from a fungus, normally only one gene will be associated with a transcriptional initiation regulatory region, so that each gene will have its own independent transcriptional initiation regulatory region. Where cDNA is employed, it will be necessary to provide an appropriate transcriptional initiation regulatory region, depending on the host m.o. used for subsequent expression.

The genes of interest may be obtained at random from a gene library (e.g., genomic or cDNA library) of a high-yielding β-lactam producing strain or its wild-type ancestor, or may be selected among a subset of the library which contains genes which may be rate-limiting in antibiotic biosynthesis. Particularly valuable genes include those which are specifically expressed during antibiotic biosynthesis, including the genes encoding β-lactam biosynthetic enzymes known in the art, e.g. tripeptide synthetase (ACVS), cyclase (IPNS), acyltransferase (AT), epimerase, expandase, hydroxylase, transacetylase, transcarbamoylase, methoxylase. Preferably genes encoding both isopenicillin N synthetase and acyltransferase are dosed or expressed in higher amounts resulting in higher yields of the desired antibiotic in the transformed fungus.

It will be appreciated by those skilled in the art, that the genes to be expressed in a β-lactam producing host may either carry their own native promoter sequence which is recognized by an RNA polymerase of the host cell, or may be ligated to any other suitable promoter, e.g. that of a different β-lactam biosynthetic gene or that of a glycolytic gene such as phosphoglycerate kinase, glyceraldehyde phosphate dehydrogenase, triose phosphate isomerase, or that of the translational elongation factor, Ef-Tu, or the like.

Such a promoter may be employed to influence regulation of expression of one or more genes encoding said enzymes. This will lead to an increased production of the antibiotic after transformation, since penicillin production is now also possible under conditions that in the untransformed host strain do not lead to penicillin production, e.g. glycolytic enzymes are expressed in the presence of glucose, while the production of penicillin, on the other hand, is repressed in the presence of glucose (J. F. Martin, vide supra). By bringing the expression of penicillin biosynthetic genes under the control of a promoter of a glycolytic gene, the genes can also be expressed in the presence of glucose and hence penicillin can be produced early in the fermentation, when a high concentration of glucose is required for the generation of a sufficient amount of mycelium. Also the selection marker can be brought under control of such a promoter.

For transformation of Penicillium, constructs are employed including at least one marker for selection of transformed cells and, preferably, for enhancing maintenance of the integrated DNA. Therefore, the vector preferably includes a DNA sequence known to enhance transformation efficiencies. An example of such a DNA sequence is the "ans"-element, isolated from *Aspergillus nidulans* (cf. Ballance and Turner, Gene 36 (1985) pp. 321–331). Our copending patent application (vide supra) provides a DNA sequence, isolated from the genome of *P. chrysogenum*, that has been identified as a sequence with an effect similar to the effect of the "ans" sequence. Since this sequence is native to *P. chrysogenum*, it can be used to increase transformation efficiencies in *P. chrysogenum*. The DNA sequence encompasses the *P. chrysogenum* pyrG gene and can be used either alone, in combination with a pyrG-host, in which case said DNA sequence provides both the selection for transformants and the transformation enhancing effect (cf. EP-A-260762), or in combination with another selection marker, e.g. a gene encoding resistance to a biocide, such as phleomycin. In the latter case selection for transformants and the transformation enhancing effect are provided by two separate DNA sequences and the sole function of the pyrG element is to enhance transformation frequencies.

Useful markers for the selection of transformant clones may be homologous or heterologous biosynthetic genes capable of complementing an auxotrophic requirement of the host cell, caused by a defect in a metabolic route to an amino acid, e.g. arginine, a nucleotide precursor, e.g. uracil, and the like.

The structural gene providing the marker for selection may be native to the wild-type Penicillium host or a heterologous structural gene which is functional in the host. For example, structural genes coding for an enzyme in a metabolic pathway may be derived from Penicillium or from other filamentous fungi, e.g. Aspergillus, Neurospora, Podospora, or yeasts, where the structural gene is functional in the Penicillium host and complements the auxotrophy to prototrophy.

The complementing structural gene may be derived from a metabolic pathway, such as the synthesis of purines or pyrimidines (nucleosides) or amino acids. Of particular interest are structural genes encoding enzymes in the pyrimidine pathway, e.g. the gene encoding the enzyme orotidine-5'-phosphate decarboxylase (pyrG or pyr4). Other genes of 13 interest are amino acid biosynthetic genes, e.g. ornithine carbamoyl transferase (argB) and arginino-succinate lyase (arg4). The use of the above mentioned selection markers is provided in EP-A-260762.

Instead of auxotrophic markers, fermentation markers may be used, such as the capability of using amides as a sole source of carbon or nitrogen, growth on various sugars, e.g. galactose or the like.

Furthermore, genes encoding resistance to biocides may be used, such as hygromycin, gentamicin, phleomycin, glyphosate, bialaphos, and the like.

Constructs will be provided comprising the sequence of interest, and may include other functions, such as replication systems in one or more hosts, e.g. cloning hosts and/or the target host for expression of the secondary metabolite; one or more markers for selection in one or more hosts, as indicated above; genes which enhance transformation efficiency; or other specialized function.

The construct will contain at least one gene, preferably two or more genes. The construct may be prepared in conventional ways, by isolating other desired genes from an appropriate host, by synthesizing all or a portion of the genes, or combinations thereof. Similarly, the regulatory signals, the transcriptional and translational initiation and termination regions, may be isolated from a natural source, be synthesized, or combinations thereof. The various fragments may be subjected to endonuclease digestion (restriction), ligation, sequencing, in vitro mutagenesis, primer repair, or the like. The various manipulations are well known in the literature and will be employed to achieve specific purposes.

The various fragments may be combined, cloned, isolated and sequenced in accordance with conventional ways. After each manipulation, the DNA fragment or combination of fragments may be inserted into the cloning vector, the vector transformed into a cloning host, e.g. *E. coli*, the cloning host grown up, lysed, the plasmid isolated and the fragment analyzed by restriction analysis, sequencing, combinations thereof, or the like. *E. coli* may also be used as a host for expression of the genes of interest with the aim to produce high amounts of protein.

Various vectors may be employed during the course of development of the construct and transformation of the host cell. These vectors may include cloning vectors, expression vectors, and vectors providing for integration into the host or the use of bare DNA for transformation and integration.

The cloning vector will be characterized, for the most part, by a marker for selection of a host containing the cloning vector and optionally a transformation stimulating sequence, may have one or more polylinkers, or additional sequences for insertion, selection, manipulation, ease of sequencing, excision, or the like.

Expression vectors will usually provide for insertion of a construct which includes the transcriptional and translational initiation region and termination regions; alternatively the construct may lack one or both of the regulatory regions, which will be provided by the expression vector upon insertion of the sequence encoding the protein product.

The DNA encoding enzyme(s) of interest may be introduced into a Penicillium host in substantial accordance with the procedure as described in EP-A-260762.

Efficient transformation of Penicillium is provided to produce transformants having one or more structural genes capable of expression, particularly integrated into the host genome (integrants). DNA constructs are prepared which allow selection of transformed host cells. Conditions are employed for transformation which result in a high frequency of transformation, so as to ensure selection and isolation of transformed hosts expressing the structural gene(s) of interest. The resulting transformants provide for stable maintenance and expression of the integrated DNA. It will be appreciated that the transformed host according to the invention can be used as starting strain in strain improvement processes other than DNA mediated transformation, for instance, protoplast fusion, mass mating and mutation. The resulting strains are considered to form part of the invention.

The genes of interest to be introduced by transformation may form an integral part of the transformation vector, but it will often be more convenient to offer these genes on a separate vector in the transformation mixture, thus introducing the said genes by cotransformation along with the selective vector, which is a fairly efficient process in filamentous fungi (e.g. P. J. Punt et al., Gene 56 (1987) pp. 117–124; K. Wernars et al, Mol. Gen. Genet. 209 (1987) pp. 71–77; I. E. Mattern et al., Mol. Gen. Genet. 210 (1987) pp. 460–461).

As a result of the transformation, there will be at least one copy of the gene(s) of interest frequently two or more, usually not exceeding about 100, more usually not exceeding about 10. The number will depend upon whether integration or stable episomal maintenance is employed, the number of copies integrated, whether the subject constructs are subjected to amplification and the like.

Several methods are known in the art for the isolation of genes of interest from a genomic library of a selected species (e.g. Maniatis et al., Molecular cloning, 1982, a laboratory manual). We have used the method of differential screening for the isolation of genes involved in the biosynthesis of penicillin. To this end, mRNA was isolated from lactose-grown (producing) and glucose-grown (non-producing) mycelium. A labelled cDNA probe was synthesized from both mRNA populations, and after enrichment of the producing cDNA probe (by elimination of all cDNA's that hybridize to non-producing mRNA) genomic clones have been isolated that only hybridize to the producing cDNA probe. The details of the procedure are given in Example 2. A large number of the clones thus isolated appear to encode the penicillin biosynthetic enzyme isopenicillin N synthetase (IPNS or cyclase).

Furthermore, among the clones, several copies of the gene encoding the side-chain exchanging enzyme (acyltransferase) are found to be present. This was proven with experiments where a DNA probe was employed, based on the amino-terminal peptide sequence of the purified enzyme. The identity of these clones is biochemically and biologically verified. The nucleotide and deduced amino acid sequence of the acyltransferase gene are specified in FIG. 3 (SEQ ID NO: 1) (SEQ ID NO: 2). Surprisingly, the genes encoding the isopenicillin N synthetase and acyltransferase enzymes are present together on one DNA fragment. This was demonstrated by hybridization of a genomic library of *P. chrysogenum* in the lambda vector EMBL 3 with separate probes, specific for each of these genes. Identical clones hybridize separately with both probes.

Figure 2:
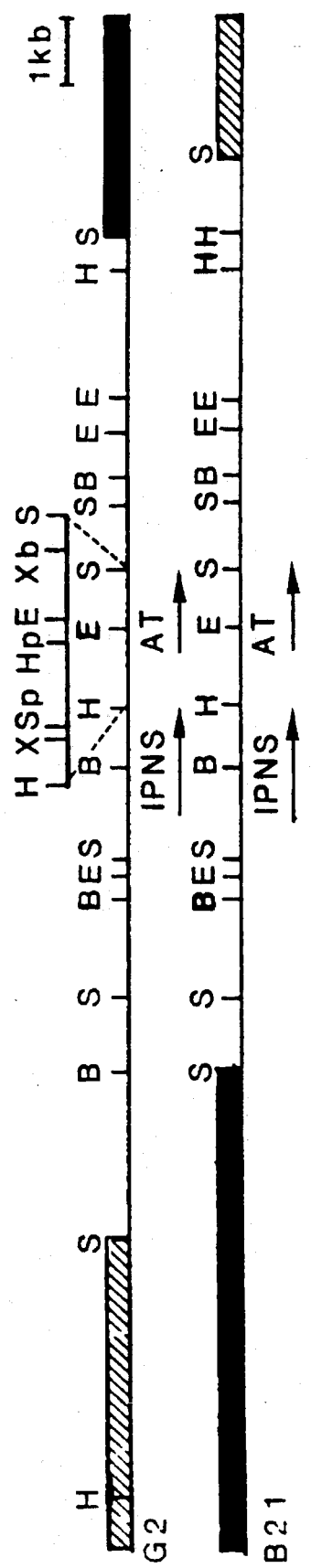

Moreover, after construction of a physical map of one genomic lambda clone, and hybridization of restriction digests of the lambda clone with separate probes for both of the genes, the genomic organization was shown to be such as depicted in FIG. 2 (clones B21 and G2). The presence of both genes on one large DNA fragment allows construction of *P. chrysogenum* strains with a higher dosage of both the isopenicillin N synthetase and acyltransferase genes, without disturbing the relative organization or the balanced expression of both genes. Moreover, the introduction of multiple copies of the large DNA fragment allows expression of both genes on the DNA fragment in their natural environment with upstream and downstream sequences that are identical to the normal situation.

Both the balanced expression and the maintenance of the natural environment prove to be beneficial for the efficiency of gene expression and hence of penicillin production, as is exemplified by an improved yield of penicillin (up to 40%) in transformants that contain a DNA construct that comprises both the AT and IPNS gene, hereinafter referred to as the [IPNS plus AT] gene cluster. Hence the clustering of the genes encoding AT and IPNS has been advantageously applied in strain improvement of Penicillium. Introduction of a DNA construct that contains only the IPNS gene did not result in improved production of penicillin (Skatrud et al, vide supra).

Figure 8:
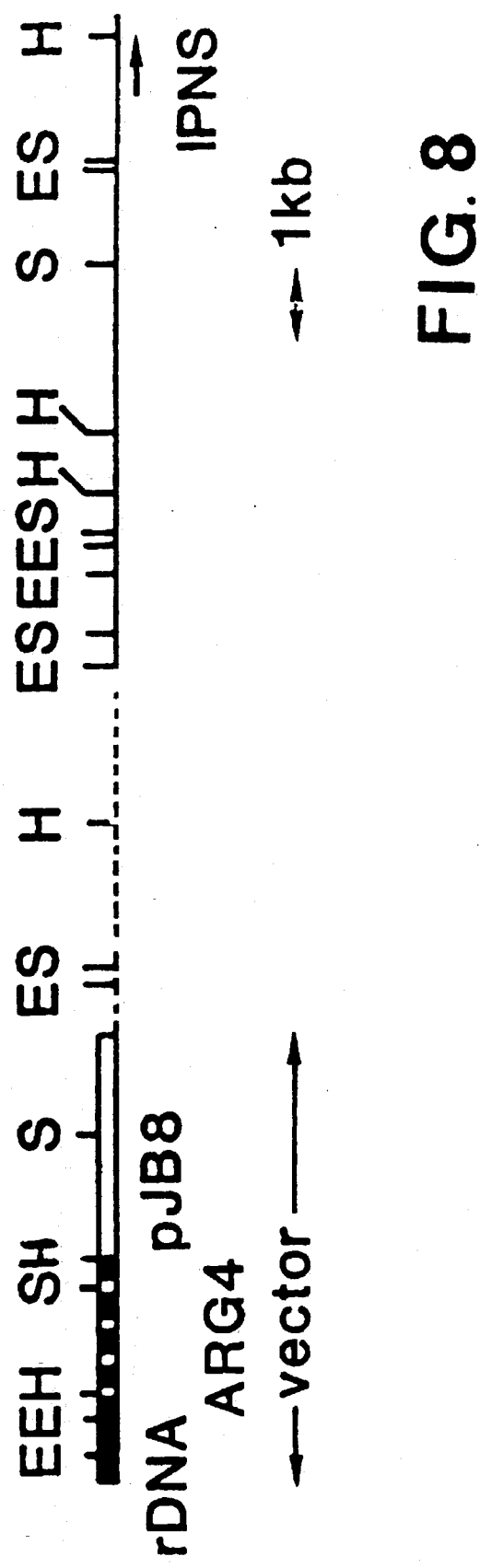

The present invention moreover provides the advantageous application of the isolation of the [IPNS plus AT] gene cluster in the isolation of another gene(s), involved in the β-lactam antibiotic biosynthesis, by chromosome walking (i.e. the technique to isolate, starting from one recombinant clone, other recombinant clones that are adjacent to the starting clone and that contain overlapping information from the genome). This is exemplified by the isolation of a cosmid clone, based on homology with the IPNS gene, and by the complementation using said cosmid clone of nonproducer mutants known to contain the enzyme activities encoded by the [IPNS plus AT] gene cluster. Therefore, the clustering of the IPNS and AT genes has been successfully applied to isolate another gene involved in the biosynthesis of penicillin, Viz, the ACVS gene. Said ACVS gene(s) is also clustered to the [IPNS plus AT] gene cluster and is present on cosmid HM193. In order to clearly define the invention, reference is made to FIG. 8, where a physical map of said cosmid is given. Moreover the cosmid clone has been deposited as CBS 179.89. It should be understood that FIG. 8 indicates the approximate positions of the restriction enzyme cleavage sites, as determined in sizing experiments using agarose gel electrophoresis, and is not necessarily intended to show all the possible restriction sites present on the DNA illustrated. The presence of another gene in cosmid HM193, e.g. encoding a regulatory protein, cannot be excluded yet. The gene encoding ACVS being isolated, the penicillin biosynthetic pathway (cf. FIG. 1) has been cloned and can be introduced into any microorganism, e.g. yeast.

The present invention is further exemplified by transforming *Penicillium chrysogenum* with genes that are specifically expressed under conditions where the antibiotic is synthesized, and which encode gene products catalyzing biosynthetic reactions leading to the said antibiotics.

One such enzyme, acyltransferase (hereinafter referred to as AT), catalyzes the final step in penicillin biosynthesis, i.e. the exchange of the aminoadipyl moiety of isopenicillin N with a hydrophobic acyl side chain precursor, e.g. phenylacetic or phenoxyacetic acid, thus yielding penicillin G or V, respectively.

The acyltransferase gene of *P. chrysogenum* is provided, including the nucleic acid sequence, conservative mutations, where the sequence encodes the same amino acid sequence, but may have as many as 30% different bases, more usually not more than about 10% different bases, or mutations which are non-conservative, where fewer than about 10%, more usually fewer than about 5%, and preferably not more than about 1% of the amino acids are substituted or deleted, and there are fewer than 5% of inserted amino acids, where the percent is based on the number of naturally occurring amino acids. In addition, fragments of both the nucleic acid encoding the enzyme, usually at least about 9 codons, more usually at least about 15 codons may be employed, as well as their expression products, as probes, for the production of antibodies, or the like. The probes may be used to identify the enzyme in other species by employing the nucleic acids for hybridization or the antibodies for identification of cross-reactive proteins.

Another enzyme, ACVS, catalyzes the first step in the biosynthesis of the β-lactam antibiotics penicillin, cephalosporin and cephamycin, i.e. the condensation of three amino acids, L-α-aminoadipic acid, L-cystein and L-valin, into the tripeptide δ-(L-α-aminoadipyl)-L-cysteinyl-D-valine. The ACVS gene is provided in the form of cosmid HM193. Parts of this cosmid, or the entire cosmid, may be used as a hybridization probe in order to identify DNA fragments in other species that also code for the ACVS enzyme. The clone may also be used in hybrid-arrested in vitro translation experiments, whereby as a first step an mRNA population is isolated that has a sufficient homology to the clone to hybridize to it. The second step is the isolation of said mRNA population and subsequent translation into a functional protein, using in vitro transcription systems known in the art. The protein thus isolated can e.g. be used for activity tests or for the production of antibodies.

The isolation of the AT-, ACVS-, Y- and other penicillin bisynthetic genes allows for the identification of regulatory elements of the individual genes such as a promoter, an upstream activating sequences (UAS), a terminator and the like. This can be achieved by sequence comparison of the genes amongst themselves and by comparison with the sequence as obtained for the isopenicillin N synthetase biosynthetic gene and other related genes. This latter comparison, moreover, may disclose the specific nature of the regulation of the gene expression of the group of penicillin biosynthetic genes.

Identification of such a "penicillin biosynthetic regulatory element" leads to identification of specific regulatory proteins by means of standard techniques as gel retardation, cross-linking, DNA footprinting and the like. Isolation of the specific regulatory protein by affinity chromatography will result in the cloning of the gene encoding said protein and subsequent manipulation in a suitable host.

By use of the cloned AT-gene, ACVS-gene, Y-gene and other penicillin biosynthetic genes, modified enzymes may be designed and synthesized. These modifications will result in modified characteristics of the enzymes, such as a change in pH or temperature optimum, a change in stability or a change in substrate specificity. Host strains, transformed with genes encoding these modified enzymes, may be programmed to perform antibiotic synthesis under different conditions or to synthesize alternative antibiotics, e.g. ampicillin instead of penicillin.

In another aspect of the invention, the cloned genes may be used to transform host strains that do not naturally possess these enzymes. It is known that Streptomyces and Acremonium do not possess the AT-enzyme, while on the other hand Penicillium lacks the genes from the cephalosporin and cephamycin biosynthetic enzymes. Introduction of such genes into the hosts will result in biosynthesis of cephalosporin or cephamycin by penicillium or penicillin or cephalosporins with a hydrophobic side chain by Acremonium. This is further exemplified by the expression of the Penicillium chrysogenum [IPNS plus AT] gene cluster in Acremonium chrysogenum.

It is evident from the following results that secondary metabolite production can be greatly enhanced by employing screening procedures which allow for identification of DNA sequences associated with production of a secondary metabolite. By using subtraction methods in identifying specific sequences associated with secondary metabolite production, mRNA and cDNA may be isolated and identified for use as probes. Thus, fragments containing cryptic genes, which will not yet have a known function are found to greatly enhance secondary metabolite production and may be transformed into a host for production of the secondary metabolite. This procedure is specifically exemplified for penicillin.

In addition, an acyltransferase gene is provided which finds use in a variety of ways, as an enzyme for modifying β-lactam compounds, as a label, as a source of an antigen for a production of antibodies to acyltransferase, as a source for a promoter sequence, as a source to express high amounts of protein for crystallization as a template for in vitro mutagenesis to obtain an enzyme with modified characteristics, and the like. Introduction of the AT gene in the [IPNS plus AT] gene cluster leads to great enhancement of production of penicillin in transformants. The clustered genotype moreover has been enployed for the isolation of another gene(s) involved in penicillin biosynthesis, viz the gene encoding ACVS. Introduction of the gene cluster into Acremonium chrysogenum results in expression of the gene cluster and in production of penicillin by Acremonium chrysogenum.

In addition, a cosmid clone is provided which contains the gene encoding ACVS. This gene like the gene encoding AT finds use in the aforementioned applications. It is possible that other (regulatory) genes are present on cosmid HM193.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

The following examples are offered by way of illustration and not by way of limitation.

EXPERIMENTAL EXAMPLE 1

Construction of a Genomic Library of Penicillium Chrysogenum.

A genomic library of Penicillium chrysogenum (ATCC 28089) was constructed in substantial accordance with methods known in the art (T. Maniatis et al., (1982), Molecular cloning, A Laboratory Manual, Cold Spring Harbor Laboratory, N.Y.). Chromosomal DNA was extracted from Penicillium chrysogenum by forming protoplasts from the mycelium as previously described in EP-A-260762.

The protoplasts were then lysed by diluting the isotonic (0.7M KCl) suspension with four volumes of TES buffer (0.05M Tris-HCl pH 8.0, 0.1M EDTA, 0.15M NaCl). To the lysate, 1% sodium lauryl sulphate was added and the mixture was incubated at 55° C. for 30 min. After one extraction with phenol and two extractions with chloroform, the DNA was precipitated with ethanol, dried, and dissolved in TE buffer (10 mM Tris, 1 mM EDTA pH 8.0). The DNA solution was then treated with 100 μg/ml RNase at 37° C. for 1 h and subsequently with 200 μg/ml proteinase K at 42° C. for 1 h. The solution was extracted once with phenol and twice with chloroform. An equal volume of isopropanol was layered on top of the aqueous phase and the DNA was collected at the interface by spooling around a glass rod. After drying, the DNA was dissolved in TE buffer. The molecular weight of the DNA preparation thus obtained was about $10^8$. The DNA was partially digested with Sau3A, ligated to dephosphorylated EMBL 3 arms cut with BamHI (Promega Biotec, Madison Wis., USA), and packaged into bacteriophage lambda capsids using the Packagene System of Promega Biotec. All reactions were carried out in accordance with the manufacturer's recommendations except that the packaging reaction was carried out at 22° C. for 2–3 hours. Libraries were amplified by plating the packaged phages, incubating for 7–8 hours at 37° C. and eluting the phages using 4 ml of SM buffer (0.1M 23 NaCl, 0.01M $MgSO_4$, 0.05M Tris HCl pH 7.5, 0.01% gelatin) per Petri plate.

EXAMPLE 2

Isolation of Genes Specifically Expressed during penicillin biosynthesis Using a Differential Screening Procedure.

Genes that are specifically or predominantly expressed during penicillin biosynthesis were identified by probing the genomic library of Example 1 with labelled cDNA probes synthesized on mRNA templates extracted from producing (lactose-grown) and non-producing (glucose-grown) mycelia, and selecting the clones that gave predominantly a positive signal with the former (+) probe.

Messenger RNAs were isolated from cultures grown 3 or 6 days in the production medium (cf. Example 3) (+preparation) or in the same medium with the lactose replaced by glucose (−preparation). The mycelia were collected by filtration, frozen in liquid nitrogen, homogenized and the mRNA isolated using the guanidinium isothiocyanate method as described by T. Maniatis et al. (vide supra).

cDNAS were synthesized and labelled to a high specific activity with $[\alpha\text{-}^{32}P]$ dATP against both mRNA populations in a reaction mixture of 30 µl containing

| | |
|---|---|
| 12.5 mM | $MgCl_2$ |
| 50 mM | Tris-HCl pH 8.3 |
| 100 mM | KCl |
| 125 mM | DTT |
| 2 u/µl | RNasin |
| 500 µM | dGTP |
| 500 µM | dCTP |
| 500 µM | dTTP |
| 25 µM | dATP |
| 0.1 µg/ml | BSA |
| 100–200 µg/ml | poly $A^+$RNA |
| 50–60 µg/ml | oligo $dT_{12-18}$ |
| 1.2 u/µl | reverse transcriptase |
| 1.67 µCi/µl | $[\alpha\text{-}^{32}P]$ dATP | in which the PolyA$^+$ RNA and oligo-dT were mixed separately, heated to 100° C. for 1 minute, and cooled in ice water prior to adding to the reaction mixture. After 1.5 hours incubation at 42° C., 5 µl of 1 mM dATP was added and the incubation continued for 30 min. Subsequently, the reaction mixture was made 20 mM in EDTA, 40 mM in NaOH (final volume 100 µl) and heated to 65° C. After 1 hour incubation, 5 µl M Tris-HCl pH 8.3, 40 µl 0.1N HCl, 7 µg calf thymus DNA, 100 µl TES buffer (10 mM Tris, 1 mM EDTA, 1% SDS pH 7.5) and 200 µl 5M ammonium acetate were added and the DNA was precipitated with 800 µl ethanol for 16 hours at −20° C.

The precipitate was collected by centrifugation, washed with 70% ethanol, dried, and dissolved in 32.5 µl of TE buffer (10 mM Tris, 1 mM EDTA pH 8.0). The (+) cDNA preparation was then enriched for sequences specifically expressed during penicillin biosynthesis by two successive rounds (cascades) of hybridization against a (−) mRNA preparation in a reaction mixture of 75 µl containing

| | |
|---|---|
| 32.5 µl | (+) cDNA |
| 10 µl | (−) mRNA (1 µg/µl) |
| 30 µl | 1M $NaPO_4$ pH 6.8 |
| 1.5 µl | 10% SDS |
| 1 µl | 0.5M EDTA |

After incubation for 16 hours at 68° C., 102 µl of water was added (final phosphate concentration 170 mM) and the mixture passed through an hydroxylapatite column equilibrated in 170 mM phosphate at 68° C. Under these conditions, double stranded nucleic acids bind to the column whereas single stranded nucleic acids are eluted. The eluate was collected, dialyzed against TE buffer for 1.5 hours, and ethanol precipitated after addition of 4 µg carrier (calf thymus) DNA. This procedure was repeated and the final unbound cDNA was directly used as a probe to screen a genomic library of the Penicillium strain as follows:

A sample of the amplified library of Example 1 was plated onto 5 Petri plates so as to contain approximately 1500 plaques per plate. The plaques were transferred in duplicate to Gene Screen Plus filters (New England Nuclear) according to the manufacturer's recommendations. One set of filters was probed with the labelled enriched (+)cDNA preparation; the duplicate set was probed with the labelled (−)cDNA as a control.

Positive plaques were purified and subjected to a second screening. In this way, 96 plaques were selected that gave a positive signal predominantly with the (+)cDNA probe.

DNAs of recombinant phages that had given a strong or moderate signal in the initial screening were labelled with $^{32}P$ and used as probes to screen Northern blots of Penicillium RNAs isolated from producing and non-producing mycelia, in order to establish the levels of expression under both conditions. In this way the recombinant clones were divided into three groups:

Class 1 contains genes highly expressed during penicillin biosynthesis and is exemplified by clones

| | |
|---|---|
| * G2 and B21 | |
| * B9, L5 and G5 | |
| * L12 | |
| * K9 | |
| Class 2 moderately expressed, exemplified by | |
| * C12 | |
| * P3 and K11 | |
| * B13 | |
| * B20 | |
| Class 3 weakly expressed, exemplified by | |
| * G3 | |
| * G1 | * K16 |
| * L10 | * B23 |

Physical maps of the recombinant phages G2 and B21 are shown in FIG. 2. Clones G2 and B21 gave a positive hybridization signal when probed with an isopenicillin N synthetase-specific probe (S. M. Samson et al., vide supra). Surprisingly, the same clones appeared also to hybridize to an acyltransferase-specific probe (see Example 5).

EXAMPLE 3

Purification of Acyltransferase.

*Penicillium chrysogenum* strain (ATCC 28089) was inoculated (at $2\times10^6$ conidia/ml) in a complex seed medium containing: corn steep liquor (20 g/l); distiller solubles (20 g/l); sucrose (20 g/l); $CaCO_3$ (5 g/l) (pH before sterilization 5.7). After 36 hours incubation at 25 ° C., 250 rpm, the obtained culture was used to inoculate twenty volumes of complex production media containing: Corn steep solids (35 g/l); lactose (25 g/l); potassium phenylacetate (2.5 g/l); $MgSO_4.7H_2O$ (3 g/l); $KH_2PO_4$ (7 g/l); corn oil (2.5 g/l ); $CaCO_3$ (10 g/l ). After continuation of the incubation for another 48 hours, the mycelium was collected by filtration and the filter cake washed four times with cold 0.15M NaCl.

200 grams (wet weight) of mycelium were suspended in 700 ml of 0.05M Tris-HCl buffer (pH 8) containing 5 mM dithiothreitol (hereinafter referred to as TD buffer) and disrupted in a Braun desintegrator (Braun, Melsungen, F. R. G.) using Ballotini glass beads (Sigma type V, diameter 450–500 μm) for periods of 30 s at intervals of 15 s with refrigeration in an ethanol/dry ice bath. The extract was then centrifuged for 30 min. at 20,000×g. This and all following steps were carried out at 4° C. To 640 ml of the extract, 27 ml of a 10% w/v protamine sulphate solution in 0.05M Tris-HCl pH 8 was slowly added. After stirring for 45 minutes, the nucleic acid precipitate was removed by centrifugation at 20,000×g and the supernatant fractionated by precipitation with ammonium sulfate while maintaining the pH of the solution at 8.0 during the ammonium sulfate additions. The fraction precipitating between 40% and 55% saturation was dissolved in TD buffer containing 1M ammonium sulfate and applied to a phenylsepharose CL-4B column (1.8×16 cm) equilibrated with the same buffer. The column was washed with TD buffer at a flow of 5 ml/min until no more unbound proteins were released. Then the acyltransferase was eluted from the column with 40% ethylene glycol in 0.05M Tris-HCl pH 8.0.

The eluted fractions were assayed for acyltransferase activity by incubating at 25° C. in a reaction mixture containing 0.2 mM phenylacetylcoenzyme A, 0.2 mM 6-aminopenicillanic acid, 5 mM dithiothreitol, 0.1M Tris-HCl pH 8.0 and enzyme extract in a final volume of 200 μl. After 10 minutes the reaction was stopped by adding 200 μl methanol. The samples were centrifuged at 5000×g and the penicillin G was assayed in the supernatant by conventional microbiological or chromatographic methods.

The active fractions from the phenylsepharose column were pooled and applied to a DEAE-Sephacel column (1.5×20 cm) equilibrated with TD buffer and the acyltransferase activity was eluted with a linear (0–0.25M) gradient of NaCl in TD buffer at a flow rate of 0.25 ml/min. The pooled active fractions were precipitated with 70% ammonium sulfate and the pellet dissolved in 3 ml of TD buffer and applied to a Sephadex G-75 (coarse) column (2.6×70 cm) equilibrated with TD buffer. The acyltransferase was eluted using TD buffer at a flow of 9 ml/h and collected in the late part of the eluted fractions as a symmetrical peak of protein corresponding to acyltransferase activity. The final purification was 258-fold.

EXAMPLE 4

Determination of the Amino-Terminal Amino Acid Sequence of Acytransferase and Design of the Corresponding Oligonucleotide Probe Mixtures.

The enzyme preparation, obtained as described in Example 3 was run on an SDS-PAGE gel (U. K. Laemmli, Nature, 227 (1970) pp. 680 ff) (13% acrylamide, 50 mA). A 29 kD-band (about 10 μg of protein) was cut out of the SDS-gel and the protein was electrophoretically transferred onto a PCGM-2 membrane (polybrene impregnated glassfibre, Janssen, Beerse, Belgium), using a Multiphor II Nova blot unit (LKB; 0.8 mA/cm²; 90 min; electrode buffer 5 mM sodium borate pH 8.0). After blotting, the PCGM-membrane was washed four times with 25 mM NaCl, 10 mM sodium borate, pH 8.0 and air dried. The PCGM-adsorbed protein band thus obtained was analyzed for N-terminal amino acid sequence, using a gasphase sequenator (Applied Biosystems model 470 a). The following sequence (SEQ ID NO: 3) was determined:

thr-thr-ala-tyr-cys-gln-leu-pro-asn-gly-ala-leu-gln-gly-gln-asn-trp-asp

According to the underlined part of this amino acid sequence, the following sets of oligodeoxyribonucleotides were synthesized:

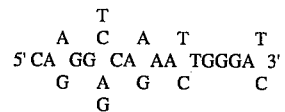

The amino-terminal amino acid sequence of a 10 kD band sometimes present in the preparation was also determined, but not used for the construction of an oligodeoxyribonucleotide probe. The sequence obtained (SEQ ID NO: 4) is:

Met-Leu-His-Ile-Leu-X-Gln-Gly-Thr-Pro-Phe-Glu-Ile-Gly-Tyr-Glu-His-Gly-Ser-Ala-Ala-Lys-Ala-Val-Ile-Ala.

EXAMPLE 5

Identification of the Acyltransferase Gene

The DNA of a number of the lambda clones of Example 2 was digested with restriction endonuclease SalI, the fragments separated on a 0.7% agarose gel, transferred to Genescreen Plus and hybridized to the [³²P]-end labelled oligonucleotide mixtures of Example 4. The clones giving a positive signal were mapped by restriction analysis using standard methods. Two representative physical maps derived for the recombinant phages, lambda B21 and lambda G2, are shown in FIG. 2. The oligodeoxyribonucleotide mixture hybridized specifically to the EcoRI/HindIII subfragment indicated on the map. This and the adjacent fragments were recloned in pTZ 18/19 (United States Biochemical Corporation) and subjected to nucleotide sequence analysis. The determined sequence (SEQ ID NO: 1) and the deduced amino acid sequence (SEQ ID NO: 2) are shown in FIGS. 3A–3C.

The amino-terminal amino acid sequence of a 10 kD band also present in the preparation was determined and found to correspond to a DNA sequence upstream of the 29 kD sequence. Therefore, AT is probably synthesized as a 40 kD protein. This notion is confirmed by the length of the AT messenger, which was demonstrated to be about 1500 bases (similar to the isopenicillin N synthetase mRNA which encodes a 38 kD protein), thus allowing for 3' and 5' untranslated regions of 100 bases.

The amino acid sequences of the 29 kD (which has been extended to Thr-Thr-Ala-Tyr-Cys-Gln-Leu-Pro-Asp-Gly-Ala-Leu-Gln-Gly-Gln-Asn-Trp-Asp-Phe-Phe-Ser-Ala-Thr-Lys-Glu-Ala) and 10 kD proteins revealed the presence of two introns. A third intron is postulated on the basis of the gross amino acid composition of the 10 kD protein (97 residues) and on the consensus sequence for its boundaries (D. J. Ballance, Yeast 2 (1986) pp. 229–236). The presence of this third intron was confirmed by primer extension and Northern blot hybridization using oligonucleotide probes from coding and non-coding regions.

EXAMPLE 6

Construction of pPS47

The phosphoglycerate kinase (pgk) gene was isolated from a Penicillium genomic library by standard methods (Maniatis; Example 1), using the corresponding yeast gene (Hitzeman et al., vide supra) as a hybridization probe.

The *P. chrysogenum* pgk promoter was cloned into pTZ18R as a 1.5 kb HindIII fragment and a clone having the desired orientation was selected.

Subsequently, the phleomycin resistance gene was cloned into the BamHI site of the polylinker of this clone as a 1.0 kb BamHI plus BglII fragment, isolated from pUT702 (Cayla, Toulouse Cedex, France). The pgk promoter was fused in frame to the phleomycin resistance gene, by looping out the sequence to be deleted using an oligonucleotide with the sequence (SEQ ID NO: 6):

5'-GGA ACG GCA CTG GTC AAC TTG GCC ATG GTG GGT
           AGT TAA TGG TAT G-3'

Moreover, this oligonucleotide introduces an NcoI site at the position of the ATG (underlined).

EXAMPLE 7

Construction of a Transformation Vector with a High Transformation Efficiency (pPS 54).

In order to obtain a transformation frequency of *P. chrysogenum* that is sufficiently high to allow introduction of genes by transformation or cotransformation with the aim of complementing or amplifying non-selectable genes involved in β-lactam biosynthesis, it is desirable to include in the transformation vector a transformation-enhancing sequence (cf. ans in Aspergillus, D. J. Ballance and G. Turner, Gene 36 (1985) pp. 321–331). Surprisingly, a transformation-stimulating sequence which is functional in *P. chrysogenum* is present on a DNA fragment containing the *P. chrysogenum* pyr G gene. This DNA fragment forms part of a 4 kb Sau3A partial fragment, cloned in the BamHI site of plasmid pUC 13 (J. Messing, in Meth. Enzymol. 101 (Acad. Press, 1983) p. 20 ff.). This plasmid is referred to as pUC13::pyrG hereinafter (see EP-A-260762).

The 2.4 kb EcoRI fragment was included in a plasmid (pPS47) containing the phleomycin-resistance gene of *Streptoalloteichus hindustanus* under the control of the promoter of the phosphoglycerate kinase (pgk) gene from *P. chrysogenum*. The resulting construct is pPS 54.

The stimulatory effect of the pyrG fragment on the frequency of transformation is shown in Table 1 below:

TABLE 1

| plasmid | transformants/µg DNA |
| --- | --- |
| pPS 47 (phleo$^R$) | 37 |
| pPS 54 (phleo$^R$, pyrG) | 186 |

EXAMPLE 8

Biological and Biochemical Verification of the Identity of the AT Clones.

The identity of the AT clones was biologically verified by complementation of an acyltransferase-negative mutant of *P. chrysogenum* ATCC 28089, npe 8.

$2\times10^7$ protoplasts of an uracil-requiring derivative of strain ATCC 28089 npe 8, ATCC 28089 npe 8 pyrG (CBS 512.88), were cotransformed with a mixture of 5 µg of the selective plasmid pUC 13:: pyrG and 15 µg of lambda B21 DNA as described previously (EP-A-260762).

Several hundreds of transformants were obtained, of which the conidia were collected and plated onto the complex production medium of Example 1 at a density of 1–10 colonies per petri dish. After 3 days incubation at 25° C., the plates were overlayered with a spore suspension of a penicillin-sensitive *Bacillus subtilis* indicator strain and incubated overnight at 30° C. to determine the size of the inhibition zones in the bacterial lawn.

Most (75%) of the transformants showed very small haloes, similar in size to the penicillin non-producing recipient stain npe 8 pyrG. The remaining 25% showed large inhibition zones comparable to those of the wild-type strain, ATCC 28089. It was concluded that the former class had received only the selective plasmid pUC 13::pyrG, whereas the latter had received both pUC 13:: pyrG and lambda B21, which restores penicillin productivity.

For several transformant clones from both groups, the level of AT-activity in cell-free extracts was determined as follows: Mycelia were collected after two days growth as described in Example 3, washed, frozen in liquid nitrogen and pulverized. For each assay, 2.5 grams of ground mycelium was suspended in 50 mM potassium phosphate buffer (pH 8.0) containing 5 mM dithiothreitol and 5 mM EDTA (final volume 12.5 ml) and stirred for 25 minutes. The cell-free extract was obtained by centrifugation of the suspension (5 minutes at 1000×g).

AT-activity was assayed by incubating 2 ml of cell-free extract with 0.1 ml dithiothreitol (10 mg/ml), 0.2 ml 6-aminopenicillanic acid (10 mg/ml) and 0.2 ml phenylacetyl-coenzyme A solution (20 mg/ml) at 25° C.

After 15 or 30 minutes, the reaction was stopped by adding an equal volume of methanol and the sample centrifuged (20 minutes at 5000×g). The supernatant was then assayed for penicillin G formed by chromatographic (HPLC) methods known in the art. The results of a typical experiment are shown in Table 2 below. These data show that in transformed strains (3) and (4) the level of AT activity is increased 2–3 fold over that of the wild-type (5), consistent with the increased gene dosage.

Figure 6A:
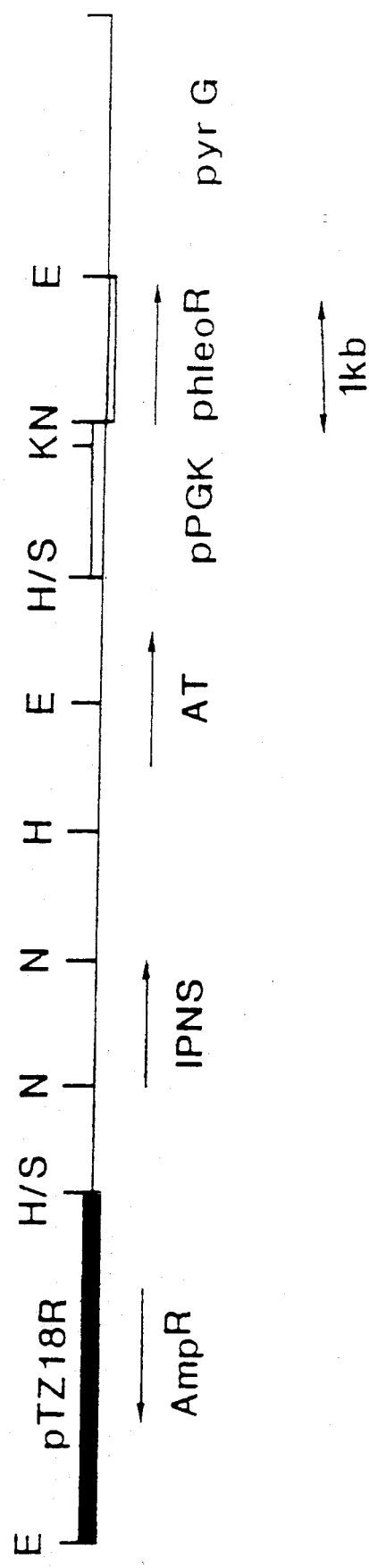
Figure 6B:
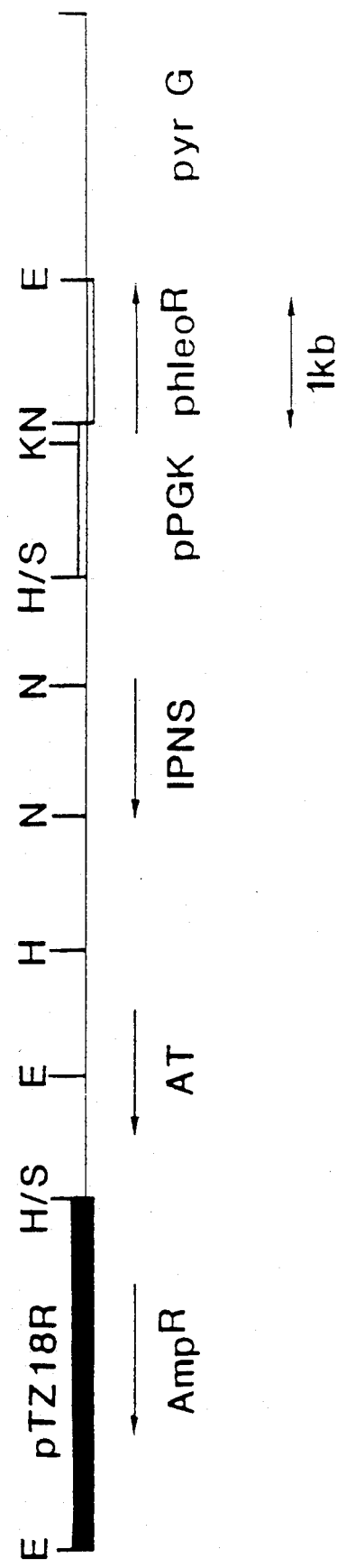
Figure 7A:
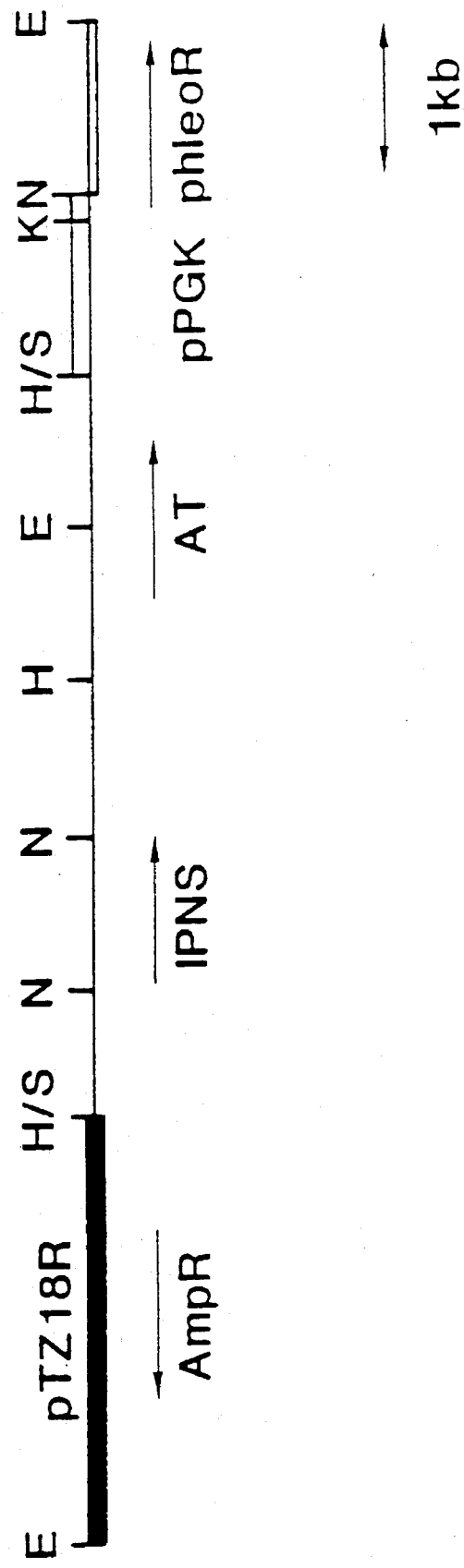
Figure 7B:
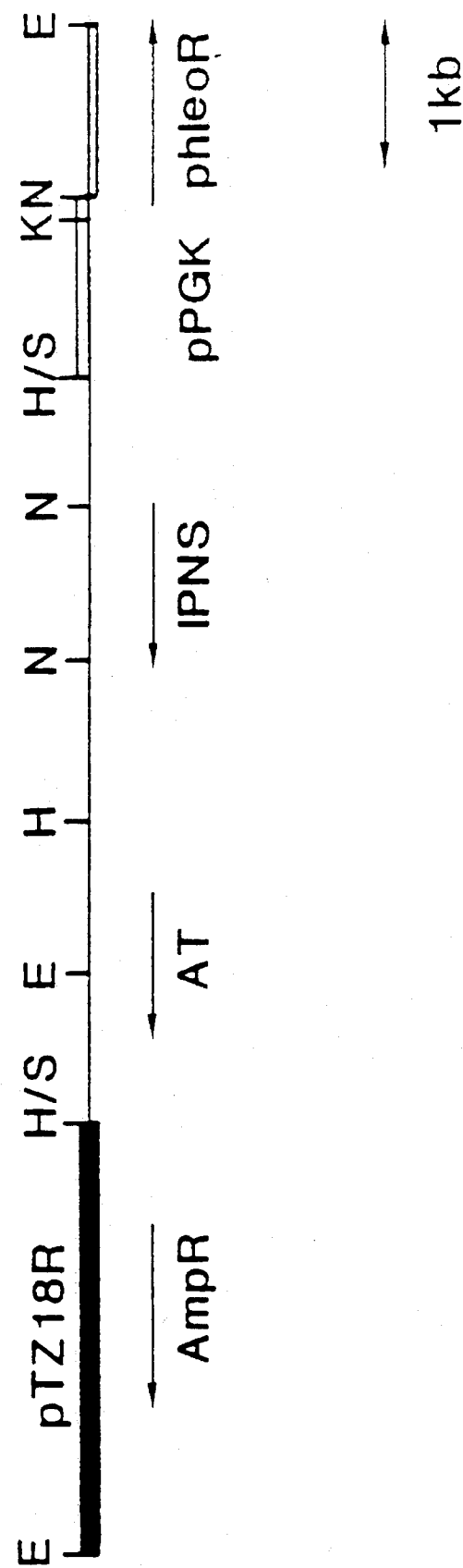

The IPNS plus AT cluster was subcloned into pPS54, yielding pGJ01 A and B (cf. FIG. 6) and into pPS47 yielding pGJ02 A and B (cf. FIG. 7). A SalI fragment of 5 kb was made blunt by the action of T4 DNA polymerase and ligated into the unique HindIII site of pPS54 or pPS47, after treatment of this vector with T4 DNA polymerase.

TABLE 2

| STRAIN | TRANSFORMED WITH: | HALO: | UNITS* PEN-G FORMED PER MG PROTEIN, | | NUMBER OF AT COPIES AS ESTIMATED BY SOUTHERN HYBRIDIZATION |
|---|---|---|---|---|---|
| | | | AFTER 15 minutes | AFTER 30 minutes | |
| 1) CBS 512.88 | pUC 13::pyrG | – | passes test | 0.9 | 1** |
| 2) idem | pUC 13::pyrG plus lambda B21 | – | 1.7 | 1.1 | 1** |
| 3) idem | idem | + | 11.9 | 9.5 | >1 |
| 4) idem | idem | + | 10.8 | 7.0 | >1 |
| 5) ATCC 28089 | not transformed | + | 4.5 | 2.7 | 1 |

*relative AT activity in extract.
**inactive by mutation

EXAMPLE 9

Increased Penicillin Production in a Host Strain Transformed with the Cryptic Gene Y.

To show the effect of the genes identified herein as involved in penicillin production, the gene dosage of one of these genes was increased in a Penicillum host strain. To this end the gene "Y", contained in lambda clones B9, L5 and G5, was subcloned as a 3.0 kb DamHi plus SphI fragment into pPS47. The resulting construct, pRH05 was transformed to P. chrysogenum Wis 54-1255 (ATCC 28089) and phleomycin resistant clones were isolated. Several clones were tested for penicillin production in shake flasks.

The results obtained for one transformant isolated are shown in Table 3 below.

TABLE 3

| strain | relative production of penicillin |
|---|---|
| ATCC 28089 | 100 |
| ATCC 28089::pRH05 | 122 |

The increased gene dosage of gene Y in the transformant, as compared to the untransformed host, was confirmed by Southern blot analysis. Hence the increased gene dosage of gene Y, a cryptic gene, isolated by the method of the invention, results in a substantial increase in penicillin production.

The transcript size for gene Y has been determined by Northern blot hybridization: the transcript is about 1.0 kb long.

EXAMPLE 10

Increased Penicillin Production by a Host Transformed with pGJ02A

Figure 9:
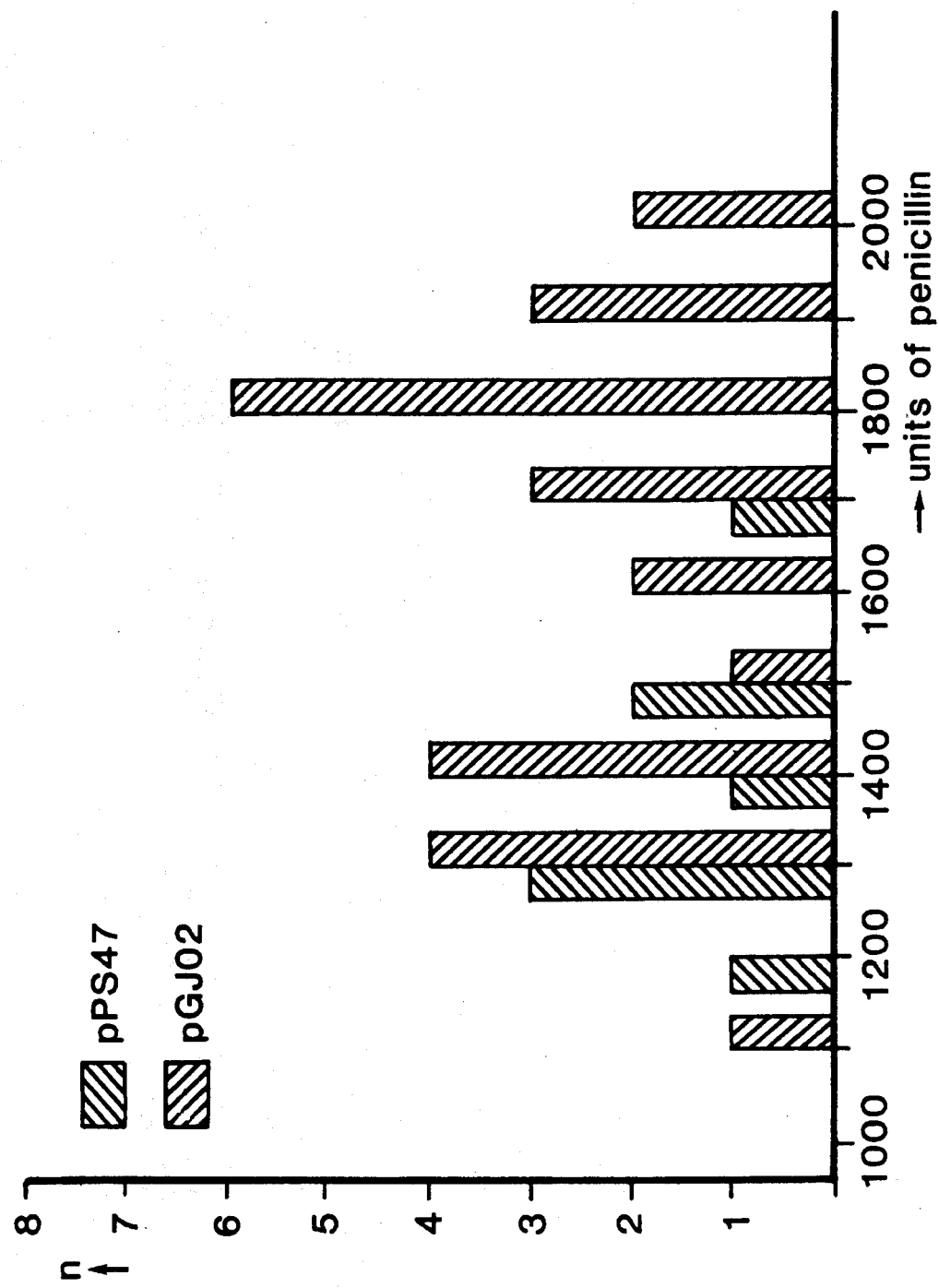

To study the effect on the production of penicillin of the [IPNS plus AT] gene cluster, as opposed to the IPNS gene alone (vide supra), $2 \times 10^7$ protoplasts of strain ATCC 28089 (=Wis54–1255) were transformed with pGJ02A (FIG. 7A) using the procedure as described in European patent application EP-A-260762. Transformants were selected using a phleomycin concentration of 30 µg/ml. About one hundred transformants and a similar number of control transformants (transformed with only the vector pPS47) were analyzed for production using the bioassay as described in Example 7. Twenty six transformants that produced a halo with a diameter that was significantly larger than that of the control transformants, were analysed for production in shake flasks. Penicillin production of these transformants was compared with the average of the penicillin production of eight control transformants: the average production of penicillin of the twenty six transformants is 18% above the average production of the control transformants, while two selected transformants were found to produce about 40% more penicillin than the average control transformants. A graphic representation is given in FIG. 9. Therefore, the [IPNS plus AT] gene cluster has been successfully applied in strain improvement of P. chrysogenum.

EXAMPLE 11

Construction of a Cosmid Library of Penicillium chrysogenum

Figure 4:
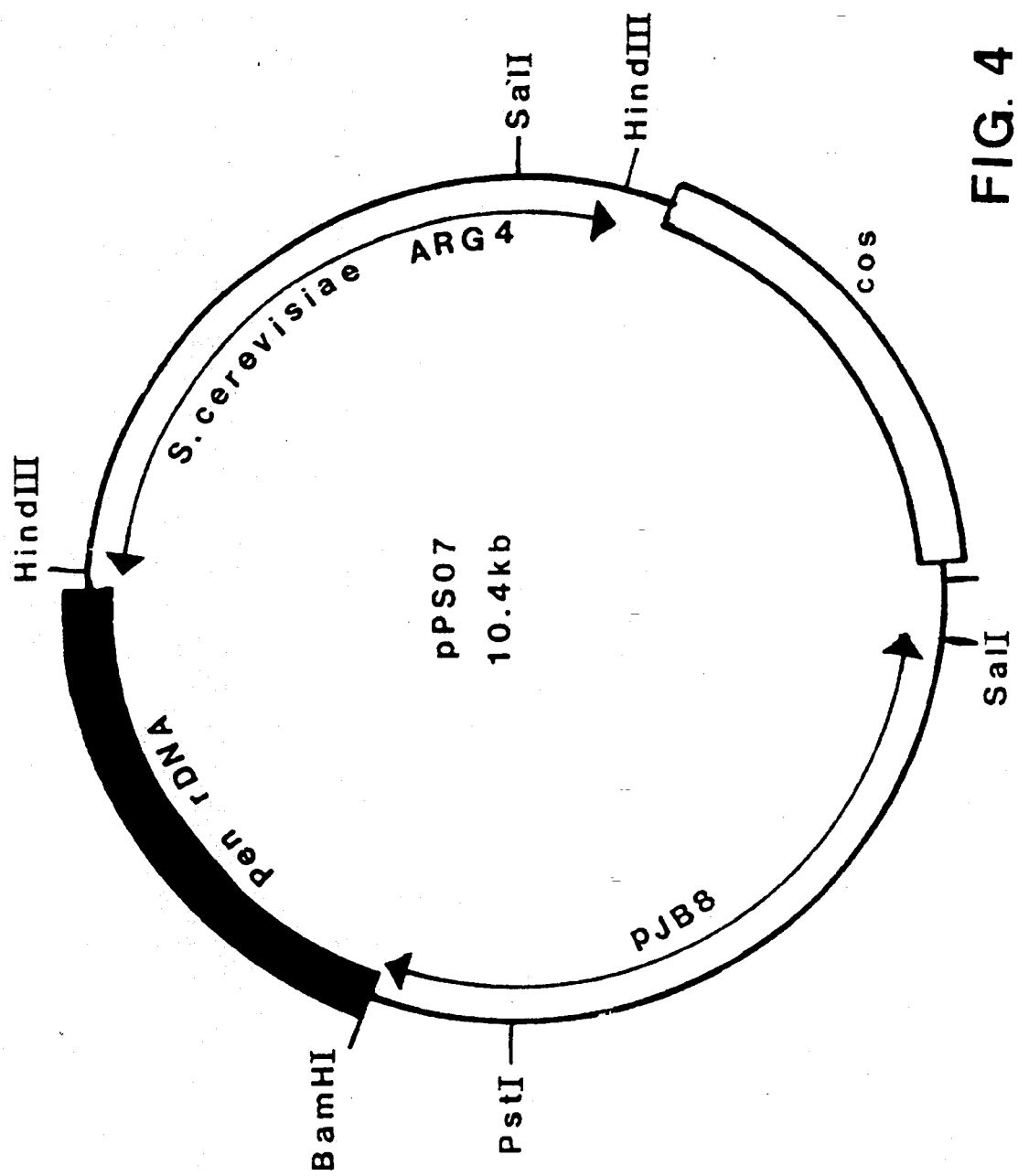
Figure 5:
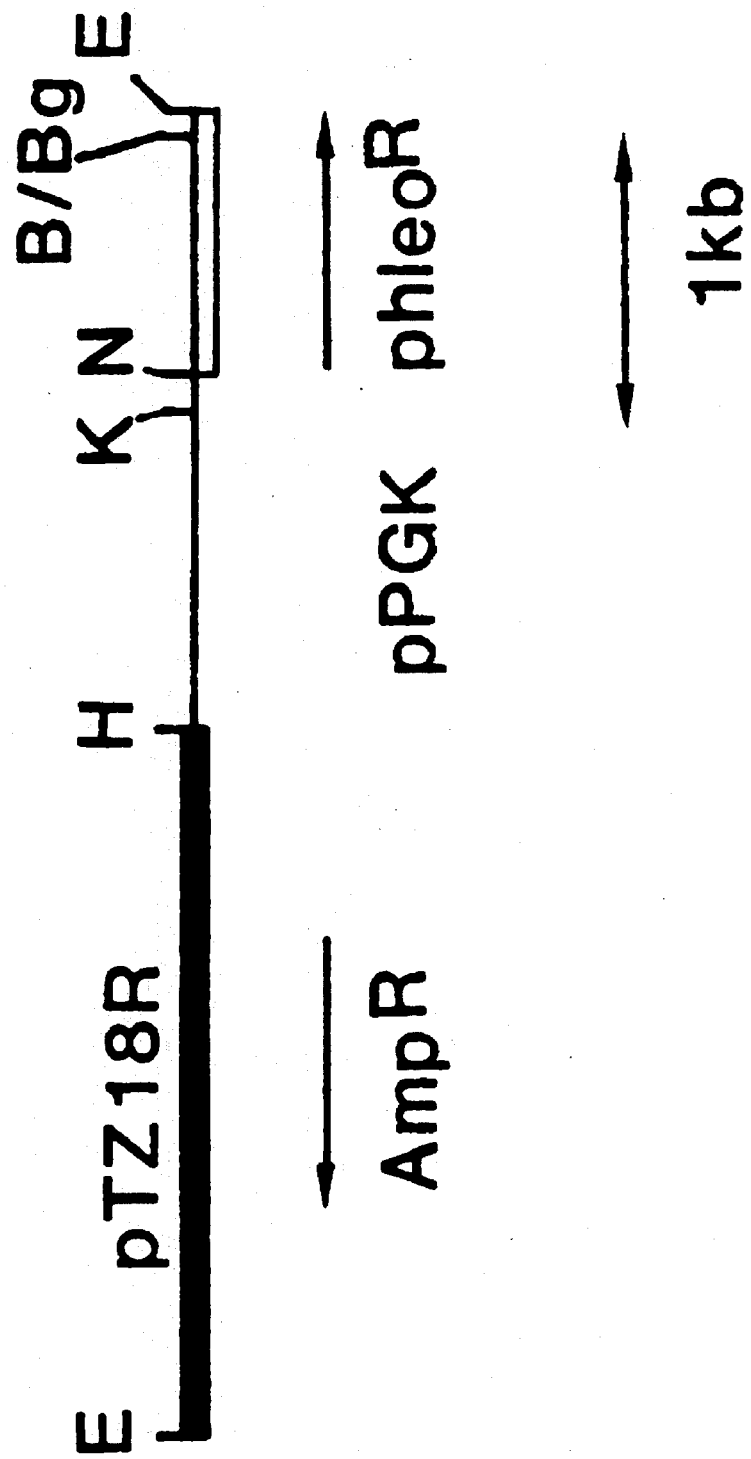

Chromosomal DNA of P. chrysogenum was isolated and treated as described in Example 1. After partial digestion of the DNA, partials of 20–35 kb in size were isolated and ligated into the BamH I digested cosmid vector pPS07 (see EP-A-0260762; cf. FIG. 4) using standard protocols (e.g. Maniatis et al, vide supra). The ligation mixture was packaged in vitro and the phage lysate was transduced into E. coli HB101 (ATCC 33694), again using methods known in the art. Fresh transductant colonies were grown in 10 ml of L-broth (per liter 10 g of NaCl, 10 g of Bacto-tryptone and 5 g of Bacto-Yeast Extract) under ampicillin selection. Cosmid DNA was isolated and the presence of insert DNA was checked by Eco RI digestion. Insertion containing cosmids were stored in microtiterplates at −20° C.

EXAMPLE 12

Isolation of Cosmid HM193, Containing the IPNS Gene

To isolate cosmid clones containing the IPNS gene and a large amount of flanking regions, the cosmid library of Example 12 was screened for clones containing the IPNS gene. A cosmid library was used, as opposed to the phage lambda library of Example 1, because cosmid vectors are known in the art to contain larger inserts (20–40 kb) than lambda vectors (9–23 kb). As probes were used two oligonucleotides based on the N-terminal aminoacid sequence of the P. chrysogenum IPNS gene: 5'-TTC GGC GAT AAC ATG GAG-3' and 5'-TTC GGC GAT AAT ATG GAG-3'. The probes were labelled using standard techniques known in the art (e.g. Maniatis et al, vide supra).

Cosmids hybridizing to the probes were isolated, and the presence of the IPNS gene was confirmed by subcloning, sequence analysis and comparison of the data to the sequence cited in L. Carr et al (vide supra). A preliminary physical map of the entire cosmid HM193 is presented in FIG. 8. The cosmid clone contains about 23 kb of DNA upstream of the IPNS gene; the clone only partly overlaps with lambda clones B21 and G2 (cf. FIG. 2).

EXAMPLE 13

Complementation of Nonproducing Mutants using Cosmid HM193

To investigate the presence of other genes than the known IPNS gene on cosmid HM193 (CBS 179.89), said cosmid was cotransformed with pGJ02A to another npe strain. Strain npe 5 (CBS 178.89) has been demonstrated to contain both IPNS and AT activity, and lacks ACVS activity. To exclude complementation based on the introduction of the IPNS gene only, transformants with construct pGJ02A only were also analysed. Transformation was performed as described herein before and (co)transformants were analysed using the bioassay as described herein before. The results are given in Table 4.

TABLE 4

| strain | # of (co)transf. tested | # of (co)transf. with halo | % |
|---|---|---|---|
| npe5 | 31 | 0* | 0 |
| npe5::pGJ02A | 72 | 1* | 1.3 |
| npe5::pGJ02A + HM193 | 19 | 5 | 26 |

*strain npe5 has a reversion frequency of about 1.5%

The data of Table 4 indicate that cosmid HM193 is able to complement the mutation of strain npe5, while plasmid pGJ02A does not complement this mutation. Therefore, another gene(s) involved in the biosynthesis of penicillin has (have) been identified starting from the IPNS gene. This gene is present on the same cosmid that also contains part of the [IPNS plus AT] gene cluster and therefore is present at a distance of less than 23 kb from the [IPNS plus AT] gene cluster.

EXAMPLE 14

Biochemical and Biological Proof of the Presence of the ACVS Gene on Cosmid HM193

To investigate whether one of the genes on cosmid HM193 encodes for ACVS, ACVS activity was determined in strain npe 5, in transformants of this strain with construct pGJ02A alone and in cotransformants of npe 5 with pGJ02A and cosmid HM193.

The strains were grown for 48 h on production medium containing lactose and 0.75% phenoxy acetic acid. Cell free extracts were prepared and ACVS activity was determined essentially as described by Van Liempt (H. van Liempt et al., J. Biol. Chem. 264 (1989), pp. 3680–3684). Extraction with buffer A was for 30 min. The amount of labelled valine used in the assay was 12.5 µCi and the reaction was stopped after 30 min. The reaction mixture was precipitated as described and subsequently applied to Porapak Q columns. The columns were washed with 2 ml equilibration buffer and eluted with 2×1 ml methanol. The ACV content was quantitated by HPLC. Samples of 100 µl were injected on a RP18 column and eluted with 10% methanol in 50 mM $KH_2PO_4$. pH 6.00 containing 0.1 mM DTT at room temperature. Flow rate was 1.0 ml/min and detection was with a Berthold LB503 scintillation detector employing a 200 µl cell. The labelled peak with a retention time identical to reduced tripeptide was collected and the amount of label was determined by counting in a liquid scintillation analyzer (Packard).

The results are shown in Table 5. Whereas no ACVS activity could be detected im cell free extracts prepared from npe 5 and from the transformant thereof with pGJ02A [IPNS plus AT], cell free extracts prepared from Wis 54-1255 and from the co-transformant with pGJ02A and HM193 contained ACVS activity. We conclude that ACVS activity has been restored in strain npe5 by the introduction of cosmid HM193. Analysis of the polypeptides present in the cell free extracts by sodium dodecyl sulphate polyacrylamide gel electrophoresis revealed the presence of a 250 kDa band in the latter strains whereas this band was absent in the former strains. The A. nidulans ACVS enzyme has a molecular weight of about this size (Van Liempt, vide supra) and we infer a similar molecular weight for the penicillium enzyme. Hence, we conclude that cosmid HM193 contains the ACVS gene.

TABLE 5

| | dpm × $10^3$ | | |
|---|---|---|---|
| strain | +ATP | −ATP | 250 kDa polypeptide |
| Wis 54-1255 | 490.8 | nd | + |
| npe5 | 3.3 | nd | − |
| npe5:pGJ02A | 2.5 | nd | − |
| npe5:pGJ02A + HM193 | 261.3 | 1.1 | + | n.d. = not determined

EXAMPLE 15

Transformation of Acremonium chrysogenum 50 ml of MMC medium (per liter: 31.6 g sucrose; 2.2 g glucose; 3 g $CaCO_3$; 0.5 g corn steep solids; 7.5 g L-asparagine; 0.22 g ammonium acetate; 15 g $KH_2P_{o4}$; 21 g $K_2HPO_4$; 0.75 g $Na_2SO_4$; 0.18 g $MgSO_4.7H_2O$; 0.06 g $CaCl_2$; 1 ml salt solution (per liter 13 g $Fe(NH_4)_2(SO_4)_2.6H_2O$; 3g $MnSO_4.4H_2O$; 3 g $ZnSO_4.7H_2O$; 0.8 g $CuSO_4.5H_2O$ )) in a 250 ml baffled shake flask were inoculated with two plates of spores, grown for 6 days on Le Page-Campbell sporulation medium (per liter: 1 g glucose; 1 g Yeast Extract; 0.5 g NaCl; 10 g $CaCl_2$; 20 g agar; pH=6.8). Cultures were incubated for 24 to 30 hrs at 28° C., shaking at 200 rpm. Mycelium was collected by filtration through a nylon filter (25 µm pore) and excess water was removed by pressing between filter papers. The isolated mycelium was resuspended at 50 mg/ml in TPC buffer (0.8M NaCl; 0.02M $MgSO_4$; 50 mM potassium phosphate buffer, pH=7) with 10 mM DTT; the mycelium was incubated with shaking at 28° C. for 90 min. Mycelium was collected by centrifugation (5 min. 2500 rpm; bench top centrifuge) and resuspended at about 25 mg/ml in TPC containing 2 mg/ml of Novozym (TM). The suspension was incubated with shaking for 2–5 hrs at 28° C. Protoplasts were filtered through 25 µm pore nylon filter and isolated by centrifugation (5 min. 2000 rpm; bench top centrifuge). The protoplast pellet was washed three times with 0.8M NaCl. Protoplasts were resuspended in 10 ml of NMC buffer (0.8M NaCl; 50 mM $CaCl_2$; 10 mM MOPS, pH=7), pelleted and resuspended in about 5×the pellet volume of NMC buffer (about 10⁸ proptoplasts/ml) and 0.1 vol. of CCM buffer (0.8M NaCl; 50 mM $CaCl_2$; 10 mM MOPS, pH=7; 18% polyethyleneglycol (PEG), Sigma) was added. For each transformation DNA and 100 μl of the protoplast suspension was added to the bottom of a 10 ml tube, the suspension was mixed carefully and stored on ice for 20 min. 500 μl of CCM buffer is added to each tube and the mixture was stored for another 20 min. at room temperature. The transformation mixture was diluted with 600 μl of NMC buffer and plated on TSA-sucrose (S. W. Queener et al, 1985, Microbiology (ASM), pp. 468–472) containing 10 μg/ml of phleomycin. Plates were incubated at 28° C. for 2–6 days. Transformants were inoculated on phleomycin containing plates; after growth spores were generated on Le Page-Campbell sporulation medium.

EXAMPLE 16

Complementation of an *Acremonium chrysogenum* Nonproducing Mutant and Production of Penicillin by Transformants of these

*Acremonium chrysogenum* strain N2 (Shirafuji et al, 1979, Agric. Biol. Chem., 4.3, 155–160; J. L. Chapman et al., Developments in Industrial Microbiology, vol. 27, p. 165, Editor G. Pierce, 1987, Society for Industrial Microbiology; F. R. Ramos et al., FEMS Microbiology Letters 35 (1986) p. 123) was transformed as described in Example 15 with lambda phage G2 (FIG. 2) containing the *P. chrysogenum* [IPNS plus AT] gene cluster. As a selective construct in the cotransformation experiment pPS47, containing the phleomycin resistance gene, was used. Strain N2 has a mutation in the IPNS gene (Shirafuji et al, vide supra) and hence produces no Cephalosporin C.

Cotransformants were isolated and tested for production. Antibiotic producing clones were isolated with a frequency of about 25% indicating that the IPNS gene of *P. chrysogenum* is being expressed in *A. chrysogenum* and that the *P. chrysogenum* enzyme can functionally replace the *A. chrysogenum* enzyme. Transformants were inoculated on complex production solid medium of Caltrider and Niss (1966; Appl. Microbiol. 14, 746–753) with and without phenylacetic acid, incubated at 27° C. for 5 days and the antibiotics produced were assayed against *Micrococcus luteus*, which is very sensitive to penicillin G but insensitive to cephalosporin C (at least up to 10 μg/ml) and *E. coli* ESS2231 which is a supersensitive strain to cephalosporin C but less sensitive to penicillin G. For *Micrococcus luteus* and *E. coli* ESS2231 see: J. M. Luengo et al., J. Antibiotics 39, 1565 (1986), M. J. López-Nieto et al., Appl. Microbiol. Biotechnol. 22, 343 (1985), G. Revilla et al., J. Baceteriol. 168, 947 (1986). The results of several transformants tested are given in Table 6. Comparison of the antibiotic active against *M. luteus* produced in the presence and absence of phenylacetic acid (PA) indicated that in many of them there is a strong stimulation of antibiotic production by PA, suggesting that penicillin G was being produced. The antibiotic produced in the absence of PA probably represents penicillin N or isopenicillin N; both compounds possess a strong antibiotic activity. A selected transformant was grown in liquid production medium (Caltrider and Niss, 1966, vide supra) supplemented with 0.8 mg/ml of PA.

The penicillin G formed was isolated by extraction with diethyl ether, after the aqueous phase had been adjusted to pH 2 using phosphoric acid.

Penicillin G can be extracted using an organic phase due to its hydrophobic side chain (PA). Cephalosporin C (which possesses a hydrophilic side chain (α-aminoadipic acid)) is not extracted into the organic phase.

After separation of the organic phase, it was in turn extracted with 0.1M potassiumphosphate buffer, pH 7.0; this extraction results in transition of penicillin G to the aqueous phase.

The aqueous phase contained antibiotic activity as judged by bioassay; *M. luteus* was more sensitive than *E. coli* to this activity. The activity could be destroyed by incubation with commercial penicillin specific penicillinase (Difco). These results indicate that indeed penicillin G is formed by the transformant. Moreover, a sample of the aqueous phase was analyzed by HPLC; the results of this assay (retention time, elution profile) identify the antibiotic compound as penicillin G. A similar experiment using fermentation broth of the host strain N2 showed that no antibiotic activity was present and hence that no penicillin G was formed by this strain. Therefore, also the *P. chrysogenum* AT gene is expressed in *A. chrysogenum* and the ability to produce penicillin G, which is normally limited to Penicillium and Aspergillus species, has been transferred to *A. chrysogenum* by transformation of the *P. chrysogenum* [IPNS plus AT] gene cluster.

TABLE 6

| | zone diameters in bioassay* | | | |
| | M. luteus | | E. coli | |
| Transformant | +PA | −PA | +PA | −PA |
| --- | --- | --- | --- | --- |
| 1 | 36 | 24 | 29 | 29 |
| 2 | 29 | 23.5 | 22 | 13 |
| 3 | 28 | 11.5 | 30 | 30 |
| 4 | 21 | 18 | 28 | 27 |
| 5 | 34 | 29 | 10 | 7 |
| 6 | 20 | 14 | 10 | 7 |
| 7 | 22 | 16 | 19 | 17.5 |
| 8 | 43 | 36 | 29 | 28 |

*note: the zone diameter is proportional to the logarithm of the amount of antibiotic that is present.

We claim:

1. A DNA construct comprising at least two genes selected from the group consisting of genes encoding isopenicillin N synthetase, acyltransferase and ACV synthetase.

2. A DNA construct according to claim 1 comprising a gene combination selected from the group consisting of (a) a combination of the genes encoding isopenicillin N synthetase and acyltransferase, (b) a combination of the genes encoding isopenicillin N synthetase and ACV synthetase, (c) a combination of the genes encoding ACV synthetase and acyltransferase, and (d) a combination of the genes encoding ACV synthetase, acyltransferase, and isopenicillin N synthetase.

3. A DNA construct according to any one of claims 1, and 2, wherein at least one of said genes is capable of complementing a β-lactam non-producing mutation.

4. A vector comprising a DNA construct selected from the group consisting of pGJ02 A, pGJ02 B and HM 193.

5. A vector comprising a DNA construct according to any one of claims 1, 2 or 4, comprising at least one member selected from the group consisting of a marker for selection in a host producing said β-lactam antibiotic and a sequence for enhancing transformation efficiency of said vector in said host.

6. A transformed host cell comprising a DNA construct according to any one of claims 1 and 3, or a vector according to claim 4.

7. A transformed host cell comprising a DNA construct according to any one of claims 1 and 3, or a vector according to claim 4 obtained by a strain improvement procedure selected from the group consisting of protoplast fusion, mass mating and mutation.

8. A transformed host comprising a vector according to claim 5.

9. A transformed host cell comprising a DNA construct according to any one of claims 1 and 3, or a vector according to claim 4 obtained by a strain improvement procedure selected from the group consisting of protoplast fusion, mass mating and mutation, wherein said host cell is selected from the group consisting of Penicillium, Aspergillus, Acremonium and Actinomycetes.

10. A transformed host according to claim 9 wherein said Penicillium is Penicillium chrysogenum.

11. A transformed host cell comprising a vector comprising a DNA construct according to any one of claims 1 and 3, or a vector according to claim 4 comprising at least one member selected from the group consisting of a marker for selection in a host cell producing said β-lactam antibiotic and a sequence for enhancing transformation efficiency of said vector in said host cell, wherein said transformed host cell is obtained by a strain improvement procedure selected from the group consisting of protoplast fusion, mass mating and mutation.

12. Progeny of a transformed host cell according to claim 6.

13. Progeny of a transformed host cell according to claim 7.

14. Progeny of a transformed host cell according to claim 9.

15. Progeny of a transformed host cell according to claim 11.

16. A method for obtaining or enhancing the production of a β-lactam antibiotic in a microbial host comprising:

preparing a DNA construct according to any one of claims 1, 2 or 4;

transforming a candidate host with said DNA construct; obtaining clones of the resulting transformants; and identifying clones having enhanced production of said β-lactam antibiotic as compared to an untransformed candidate host.

17. A method for enhancing the production of a β-lactam antibiotic comprising:

growing a host cell comprising an extra copy of at least two genes selected from the group consisting of genes encoding isopenicillin N synthetase, acyltransferase and ACV synthetase, wherein said host cell or an ancestor of said host cell is a transformant, resulting in enhanced production of said antibiotic; and isolating the resulting antibiotic product.

* * * * *